«12» United States Patent
Lu et al.

«10» Patent No.: US 11,059,810 B2
«45» Date of Patent: Jul. 13, 2021

«54» PHARMACEUTICALLY ACCEPTABLE SALT AS RENAL OUTER MEDULLARY POTASSIUM CHANNEL INHIBITOR

«71» Applicant: Jiangsu Hengrui Medicine Co., Ltd., Jiangsu (CN)

«72» Inventors: Yun Lu, Jiangsu (CN); Qiyun Shao, Jiangsu (CN); Guaili Wu, Jiangsu (CN); Jun Feng, Jiangsu (CN)

«73» Assignee: Jiangsu Hengrui Medicine Co., Ltd., Jiangsu (CN)

«*» Notice: Subject to any disclaimer, the term of this patent is extended or adjusted under 35 U.S.C. 154(b) by 26 days.

«21» Appl. No.: 16/305,644

«22» PCT Filed: Jun. 6, 2017

«86» PCT No.: PCT/CN2017/087326
§ 371 (c)(1),
(2) Date: Nov. 29, 2018

«87» PCT Pub. No.: WO2017/211271
PCT Pub. Date: Dec. 14, 2017

«65» Prior Publication Data
US 2020/0123135 A1    Apr. 23, 2020

«30» Foreign Application Priority Data
Jun. 7, 2016   (CN) .......................... 201610398233.0

«51» Int. Cl.
*C07D 405/14*   (2006.01)
*A61P 9/12*     (2006.01)
*A61P 9/04*     (2006.01)

«52» U.S. Cl.
CPC ............. *C07D 405/14* (2013.01); *A61P 9/04* (2018.01); *A61P 9/12* (2018.01)

«58» Field of Classification Search
CPC .................................................. C07D 405/14
USPC ........................................ 546/193; 514/318
See application file for complete search history.

«56» References Cited

U.S. PATENT DOCUMENTS

| | | | |
|---|---|---|---|
| 6,627,646 B2* | 9/2003 | Bakale .................... | A61P 37/08 514/322 |
| 8,673,920 B2* | 3/2014 | Pasternak ................ | A61P 3/00 514/253.11 |
| 10,364,234 B2* | 7/2019 | Li ............................ | A61P 9/04 |

FOREIGN PATENT DOCUMENTS

| | | |
|---|---|---|
| CN | 102459216 A | 5/2012 |
| CN | 104540826 A | 4/2015 |
| WO | 2010129379 A1 | 11/2010 |
| WO | 2014085210 A1 | 6/2014 |
| WO | 2016091042 A1 | 6/2016 |

OTHER PUBLICATIONS

Bernstein, "Polymorphism in . . . " p. 115-118, 272. (Year: 2002).*
Davidovich et al., "Detection of polymorphism . . . " Am. Pharm. Rev. 7(1) p. 10, 12, 14, 16, 100. (Year: 2004).*
Dean "Analytical Chem . . . " p. 10.24-10.26. (Year: 1995).*
Ivanisevic et al. "Use of X-ray . . . " Pharm. Sci. Encycl. p. 1-42. (Year: 2010).*
Seddon "Pseudopolymorph . . . " Crystal Growth &amp; design v.4(6) p. 1087 (2 pages from internet. (Year: 2004).*
Rodriguez-Spong et al., "General principles, etc.," Adv. Drug Delivery Reviews 56 241-274. (Year: 2004).*
Kirk-Othmer Encyclopedia of Chemical Technology, 8, pp. 95-147. (Year: 2002).*
Vippagunta et al., "Crystalline Solids", Advanced Drug Delivery Reviews 48 .3-26. (Year: 2001).*
Guillory (in Brittain ed.), "Polymorphism in Pharmaceutical Solids.," NY: Marcel Dekker, Inc., 1-2, 183-226. (Year: 1999).*
Braga et al., "Making crystals from . . . " J. Royal Soc. Chem. Commun. p. 3635-3645. (Year: 2005).*
CMU Pharmaceutical polymorphism, internet p. 1-3 printout Apr. 3, 2008. (Year: 2002).*
Singhal et al., "Drug Polymorphism, etc.," Advanced Drug Delivery reviews 56, p. 335-347. (Year: 2004).*
Concise Encyclopedia Chemistry, NY: Walter de Gruyter, 872-873. (Year: 1993).*
Jain et al., "Polymorphism in Pharmacy", Indian Drugs, 23(6) 315-329. (Year: 1986).*
Muzaffaretal., "Polymorphism and Drug Availability, etc.," J of Pharm. (Lahore), 1(1), 59-66. (Year: 1979).*
U.S. Pharmacopia #23, National Formulary #18,1843-1844. (Year: 1995).*
Doelker, english translation of S.T.P, Pratiques, 9(5), 399-409, pp. 1-33. (Year: 1999).*
Doelker, english translation of Ann. Pharm. Fr.,60: 161-176, pp. 1-39. (Year: 2002).*
Taday et al., "Using Terahertz, etc.," J of Pharm. Sci., 92(4), 831-838. (Year: 2003).*
Otuska et al., "Effect of Polymorphic, etc.," Chem. Pharm. Bull., 47(6) 852-8569. (Year: 1999).*
Int'l Search Report dated Jul. 25, 2017 in Int'l Application No. PCT/CN2017087326.

* cited by examiner

*Primary Examiner* — Patricia L Morris
«74» *Attorney, Agent, or Firm* — Ice Miller LLP

«57» ABSTRACT

A pharmaceutically acceptable salt as a renal outer medullary potassium channel (ROMK) inhibitor, specifically an L-tartrate and a crystal form I and crystal form II thereof, is described. The pharmaceutically acceptable salt of the ROMK inhibitor, specifically the L-tartrate, has improved bioavailability and stability.

6 Claims, 11 Drawing Sheets

PHARMACEUTICALLY ACCEPTABLE SALT AS RENAL OUTER MEDULLARY POTASSIUM CHANNEL INHIBITOR

CROSS REFERENCE TO RELATED APPLICATION

This application is a Section 371 of International Application No. PCT/CN2015/087326, filed Jun. 6, 2017, which was published in the Chinese language on Dec. 14, 2017 under International Publication No. WO 2017/211271 A1, which claims priority under 35 U.S.C. § 119(b) to Chinese Application No. 201610398233.0, filed Jun. 7, 2016, the disclosures of which are incorporated herein by reference in their entirety.

FIELD OF THE INVENTION

The present invention relates to a pharmaceutically acceptable salt of (R)-5-cyano-N-(1-(2-hydroxy-2-(4-methyl-1-oxo-1,3-dihydroisobenzofuran-5-yl)ethyl) piperidin-4-yl)-4-methoxypicolinamide.

BACKGROUND OF THE INVENTION

Increased renal salt reabsorption function can cause a risk of hypertension. On the contrary, inhibition of renal reabsorption function can promote the excretion of urine, which results in diuretic and antihypertensive effects. Common diuretics are thiazide diuretics, which are first-line antihypertensive drugs in USA that primarily act on $Na^+$—$Cl^-$ transporters. The Loop diuretics are more effective for patients with impaired renal function, and they play a role through $Na^+$—$K^+$-$2Cl^-$ transport proteins. However, both drugs can cause hypokalemia (symptoms: weakness, fatigue, muscle cramps, constipation, and heart rhythm problems, such as arrhythmia), which increases the risk of morbidity and mortality of cardiovascular diseases.

Renal Outer Medullary Potassium channel (ROMK) is also known as the inward-rectifying potassium channel 1.1 (Kir1.1). The ROMK ion channel, cooperating with the $Na^+$—$K^+$-$2Cl^-$ co-transport protein NKCC2 (responsible for NaCl transport) through the apical membrane conductance of the renal thick ascending limb (TAL), can regulate the reabsorption of $Na^+$. The ROMK was found to be directly associated with the renal secretory channel. When the ROMK gene is knocked out in mice, there is a loss of TAL and CCD 35-pS ion channels as well as a loss of the other $K^+$ channels in TAL. Batter syndrome is an autosomal recessive disease characterized by massive loss of salt in the kidneys, hypokalemia, and low blood pressure. Batter syndrome is mainly caused by mutations in the ROMK or $Na^+$—$K^+$-$2Cl^-$ co-transport proteins. The difference is that the hypokalemia of the batter syndrome caused by the mutation of ROMK is much milder compared to that caused by the mutation of $Na^+$—$K^+$-$2Cl^-$ co-transport proteins. In summary, inhibition of ROMK function can effectively inhibit the salt reabsorption function of $Na^+$—$K^+$-$2Cl^-$ co-transport proteins and promote the excretion of urine, thereby resulting in diuretic and antihypertensive effects, without causing hypokalemia.

WO2016091042, which was previously filed by the applicant and is incorporated herein by reference in its entirety, discloses a series of renal outer medullary potassium channel (ROMK) inhibitors, comprising a compound represented by the following formula, with the chemical name of (R)-5-cyano-N-(1-(2-hydroxy-2-(4-methyl-1-oxo-1,3-dihydroisobenzofuran-5-yl)ethyl) piperidin-4-yl)-4-methoxypicolinamide. Compared to other ROMK inhibitors, this compound is added with a polar group, which reduces C log P, enhances the hERG selectivity and improves safety, while maintaining the ROMK inhibitor activity.

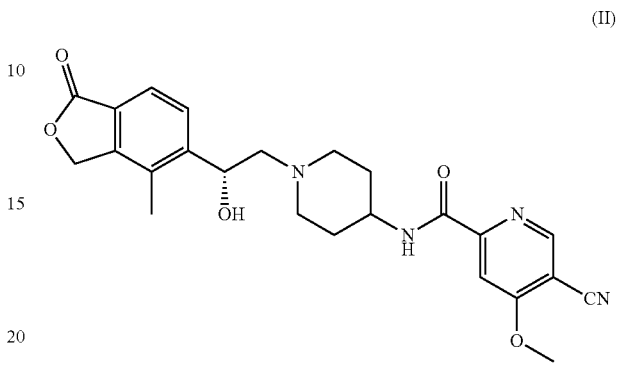

(II)

However, the compound is present in the form of a free base with poor bioavailability and stability. Therefore, it is necessary to find a suitable form for the development to solve the problem of low bioavailability and low stability. Moreover, the crystal structure of the pharmaceutically active ingredient often affects the chemical stability of the drug. Different crystallization conditions and storage conditions can lead to changes in the crystal structure of the compound, and sometimes accompanying production of other crystal forms. In general, an amorphous drug product does not have a regular crystal structure, and often has other defects, such as poor product stability, finer crystallization, difficult filtration, easy agglomeration, and poor liquidity. Therefore, it is necessary to improve the various properties of the above compound. There is a need to find a new crystal form with high purity and good chemical stability.

SUMMARY OF THE INVENTION

The present invention provides a pharmaceutically acceptable salt, in particular an acid addition salt of (R)-5-cyano-N-(1-(2-hydroxy-2-(4-methyl-1-oxo-1,3-dihydroisobenzofuran-5-yl)ethyl) piperidin-4-yl)-4-methoxypicolinamide. The bioavailability and stability can be greatly improved after salt formation.

In a preferred embodiment, the salt can be selected from the group consisting of tartrate, hydrochloride, sulfate, methanesulfonate, phosphate, citrate, maleate, fumarate, malate, benzenesulfonate, p-toluenesulfonate and hydrobromide, and most preferably L-tartrate and malate. The L-tartrate of (R)-5-cyano-N-(1-(2-hydroxy-2-(4-methyl-1-oxo-1,3-dihydroisobenzofuran-5-yl)ethyl) piperidin-4-yl)-4-methoxypicolinamide, i.e. the compound of the following formula (I), can be obtained by reacting (R)-5-cyano-N-(1-(2-hydroxy-2-(4-methyl-1-oxo-1,3-dihydroisobenzofuran-5-yl)ethyl) piperidin-4-yl)-4-methoxypicolinamide with L-tartaric acid. The hydrochloride, sulfate, methanesulfonate, phosphate, citrate, maleate, fumarate, malate, benzenesulfonate, p-toluenesulfonate and hydrobromide of (R)-5-cyano-N-(1-(2-hydroxy-2-(4-methyl-1-oxo-1,3-dihydroisobenzofuran-5-yl)ethyl) piperidin-4-yl)-4-methoxypicolinamide can be prepared by using a similar method. Since the solubility of the compound of formula (II) is low, in order to further increase its solubility, the applicant has carried out a salt formation study on the compound of formula (II), wherein the salt formation of the compound of formula (II) with tartaric acid, hydrochloric acid, sulfuric acid, methanesulfonic acid, phosphoric acid, citric acid, maleic acid, fumaric acid, malic acid, benzenesulfonic acid, p-toluenesulfonic acid, hydrobromic acid or lactic acid has been investigated. The solubility of the compound has been greatly improved after salt formation. Whether the salt is easy to form crystals etc. has also been investigated. It has an important research significance in the treatment of ROMK related diseases. During the salt formation process, the applicant has found that the reaction between lactic acid and the compound of formula (II) does not result in a salt, the ratio of fumaric acid to the compound of formula (II) and the crystal form are difficult to control when forming a fumarate, the sulfate and citrate are obviously hygroscopic, the crystal forms of phosphate are complicated and exist simultaneously, which leads to difficulty in separation, and there are many types of the crystal forms of maleate.

2) filtering the crystal, then washing and drying it.

In a preferred embodiment, the solvent in step 1) is methanol, ethanol, isopropanol or an aqueous solution of the alcohol; wherein the single solvent is preferably methanol.

In an embodiment of the present invention, the preferred mixed organic solvent is a mixed solvent of ethanol/water, and the ratio of the two is not particularly limited. In a preferred embodiment of the present invention, the volume ratio of the two is 9:1.

Crystal form II of the compound of formula (I) can be obtained under another crystallization condition, wherein the X-ray powder diffraction spectrum thereof is obtained by using Cu-Kα radiation and represented by diffraction angle 2θ angle, in which there are characteristic peaks at diffraction angle 2θ angles of 3.88, 13.00, 17.25, 25.42 and 27.79, wherein the error range of 2θ angle of each characteristic peak is ±0.2.

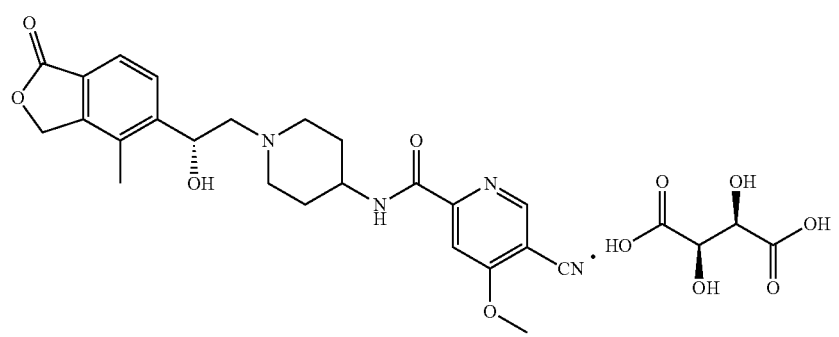

(I)

A series of crystal products of the compound of formula (I) have been obtained under different crystallization conditions, and X-ray diffraction and differential scanning calorimetry (DSC) measurements have been conducted on the obtained crystal products. It was found that a stable crystal form, which is referred to as crystal form I, can be obtained under crystallization conditions of the present invention. The DSC spectrum of crystal form I of the present application shows a melting endothermic peak at about 218.42° C. The X-ray powder diffraction spectrum, which is obtained by using Cu-Kα radiation and represented by diffraction angle 2θ angle, is shown in FIG. 1, in which there are characteristic peaks at diffraction angle 2θ angles of 3.49, 10.22, 12.27, 13.69, 15.46, 16.98, 18.04, 19.45, 23.95 and 29.44, wherein the error range of 2θ angle of each characteristic peak is ±0.2.

The present invention also provides a method for preparing crystal form I of the tartrate of (R)-5-cyano-N-(1-(2-hydroxy-2-(4-methyl-1-oxo-1,3-dihydroisobenzofuran-5-yl)ethyl) piperidin-4-yl)-4-methoxypicolinamide, comprising the following steps of:

1) adding L-tartaric acid to an appropriate amount of solvent and dissolving it under heating, then adding any crystal form or amorphous form of (R)-5-cyano-N-(1-(2-hydroxy-2-(4-methyl-1-oxo-1,3-dihydroisobenzofuran-5-yl)ethyl) piperidin-4-yl)-4-methoxypicolinamide to form a salt; wherein the solvent is selected from the group consisting of an alcohol having 3 or less carbon atoms, and a mixed solvent of the alcohol and water; and The method for preparing the crystal form II can comprise the following steps of:

1) adding any crystal form or amorphous form of the compound of formula (I), or adding L-tartaric acid and (R)-5-cyano-N-(1-(2-hydroxy-2-(4-methyl-1-oxo-1,3-dihydroisobenzofuran-5-yl)ethyl) piperidin-4-yl)-4-methoxypicolinamide to a solvent to dissolve and precipitate a crystal, wherein the solvent is a mixed solvent of isopropanol/tetrahydrofuran/water; and 2) filtering the crystal, then washing and drying it.

The recrystallization method is not particularly limited, and can be carried out by a conventional recrystallization process. For example, the material, i.e., the compound of formula (I), can be dissolved in an organic solvent under heating, and then the solution is cooled slowly to precipitate a crystal. After the completion of crystallization, the desired crystal can be obtained via filtering and drying. In particular, the crystal obtained by filtration is usually dried in a vacuum under reduced pressure at a heating condition of about 30 to 100° C., preferably 40 to 60° C., to remove the recrystallization solvent.

The present invention also provides a malate, characterized in that the chemical ratio of (R)-5-cyano-N-(1-(2-hydroxy-2-(4-methyl-1-oxo-1,3-dihydroisobenzofuran-5-yl)ethyl) piperidin-4-yl)-4-methoxypicolinamide to malic acid is 1:1, and the specific structure thereof is shown in the formula (I'):

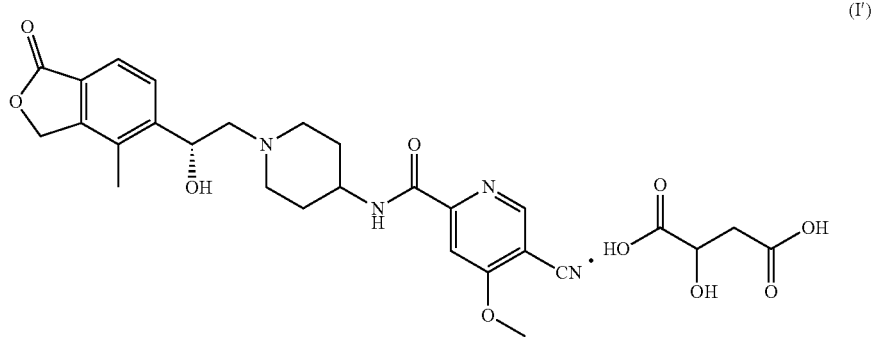 [SMILES: COc1cc(C(=O)NC2CCN(C[C@H](O)c3ccc4c(c3C)COC4=O)CC2)ncc1C#N ; O=C(O)CC(O)C(=O)O]

(I')

The present invention further provides a malate, wherein the chemical ratio of (R)-5-cyano-N-(1-(2-hydroxy-2-(4-methyl-1-oxo-1,3-dihydroisobenzofuran-5-yl)ethyl) piperidin-4-yl)-4-methoxypicolinamide to malic acid is 1:0.5, and the specific structure thereof is shown in formula (I''):

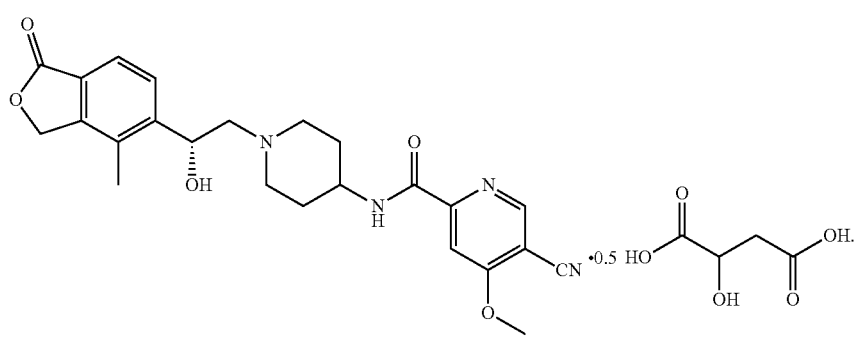

(I'')

Preferably, the crystal form 1 of the compound of formula (I') is characterized in that the X-ray powder diffraction spectrum thereof is obtained by using Cu-Kα radiation and represented by diffraction angle 2θ angle, in which there are characteristic peaks at diffraction angle 2θ angles of 6.85, 9.76, 11.81, 12.48, 13.52, 14.23, 15.29, 17.55, 17.89, 19.65, 20.25, 22.68(3.92), 23.50, 24.27, 27.83 and 28.59, wherein the error range of 2θ angle of each characteristic peak is ±0.2.

The present invention also provides a method for preparing the crystal form 1 of the compound of formula (I'), wherein the method is selected from the following preparation methods:

(1) reacting the free form of the compound of formula (I') with malic acid in a solvent or a mixed solvent, followed by stirring, precipitation, filtration and drying to obtain the desired crystal form 1; wherein the solvent is an alcohol solvent, the mixed solvent is a mixed solvent of an alcohol and water, the alcohol solvent is preferably methanol, and the mixed solvent of an alcohol and water is preferably a mixed solvent of methanol and water; and (2) adding the compound of formula (I') to a solvent, followed by pulping, filtration and drying to obtain the desired crystal form 1; wherein the solvent is a mixed solvent of an alcohol and water, the alcohol solvent is preferably methanol, ethanol or isopropanol, and the mixed solvent of an alcohol and water is preferably a mixed solvent of methanol and water or a mixed solvent of ethanol and water.

Preferably, the crystal form 2 of the compound of formula (I') is characterized in that the X-ray powder diffraction spectrum thereof is obtained by using Cu-Kα radiation and represented by diffraction angle 2θ angle, in which there are characteristic peaks at diffraction angle 2θ angles of 9.34, 10.61(8.33), 12.24, 12.78, 13.83, 14.26, 15.52, 17.83, 18.83, 19.86, 20.55, 21.72, 22.31, 22.62, 23.42, 24.78, 25.03, 25.27, 25.78, 26.02, 26.76, 27.99, 30.72, 31.19, 34.41, 36.68, 39.87 and 41.25, wherein the error range of 2θ angle of each characteristic peak is ±0.2.

The present invention also provides a method for preparing the crystal form 2 of the compound of formula (I'), characterized in that the method is selected from the following preparation methods:

(1) reacting the free form of the compound of formula (I') with malic acid in a solvent or a mixed solvent, followed by stirring, precipitation, filtration and drying to obtain the desired crystal form 2; wherein the solvent is selected from the group consisting of an alcohol solvent and a nitrile solvent, the mixed solvent is selected from the group consisting of a mixed solvent of a nitrile and water and a mixed solvent of a nitrile and an ether, preferably, the alcohol solvent is methanol or ethanol, the nitrile solvent is acetonitrile, and the ether solvent is tetrahydrofuran; and (2) adding the compound of formula (I') to a solvent or a mixed solvent, followed by pulping, filtration and drying to obtain the desired crystal form 2; wherein the solvent is selected from the group consisting of an alcohol solvent, a nitrile solvent and a ketone solvent, preferably the solvent is selected from the group consisting of an alcohol solvent and a nitrile solvent, the mixed solvent is selected from the group consisting of a mixed solvent of a nitrile and water and a mixed solvent of a nitrile and an ether, preferably, the alcohol solvent is methanol or ethanol, the nitrile solvent is acetonitrile, and the ether solvent is tetrahydrofuran.

Preferably, the crystal form 3 of the compound of formula (I') is characterized in that the X-ray powder diffraction spectrum thereof is obtained by using Cu-Kα radiation and represented by diffraction angle 2θ angle, in which there are characteristic peaks at diffraction angle 2θ angles of 9.34, 10.63, 12.79, 14.22, 15.50, 18.86, 19.93 and 25.16, wherein the error range of 2θ angle of each characteristic peak is ±0.2.

The present invention also provides a method for preparing the crystal form 3 of the compound of formula (I'), characterized in that the method is selected from the following preparation methods:

(1) reacting the free form of the compound of formula (I') with malic acid in a solvent or a mixed solvent, followed by stirring, precipitation, filtration and drying to obtain the desired crystal form 3; wherein the solvent is selected from the group consisting of an alcohol solvent and a ketone solvent, the mixed solvent is selected from the group consisting of a mixed solvent of an alcohol and water, the alcohol solvent is preferably isopropanol, the ketone solvent is acetone, and the mixed solvent of an alcohol and water is a mixed solvent of isopropanol and water; and (2) adding the compound of formula (I') to a solvent or a mixed solvent, followed by pulping, filtration and drying to obtain the desired crystal form 3; wherein the solvent is selected from the group consisting of an alcohol solvent and a ketone solvent, the mixed solvent is a mixed solvent of an alcohol and water, the alcohol solvent is preferably isopropanol, the ketone solvent is acetone, and the mixed solvent of an alcohol and water is preferably a mixed solvent of isopropanol and water.

Preferably, the crystal form A of the compound of formula (I") is characterized in that the X-ray powder diffraction spectrum thereof is obtained by using Cu-Kα radiation and represented by diffraction angle 2θ angle, in which there are characteristic peaks at diffraction angle 2θ angles of 9.95, 12.12, 12.68, 13.56, 14.73, 15.32, 16.20, 17.27, 18.74, 20.00, 21.57, 22.82, 23.22, 24.35, 24.63, 25.42, 27.13, 28.15, 30.01, 30.30, 32.92 and 34.97, wherein the error range of 2θ angle of each characteristic peak is ±0.2.

The present invention also provides a method for preparing the crystal form A of the compound of formula (I"), characterized in that the method is selected from the following preparation methods:

(1) reacting the free form of the compound of formula (I") with malic acid in a solvent or a mixed solvent, followed by stirring, precipitation, filtration and drying to obtain the desired crystal form A; wherein the solvent is an alcohol solvent, the mixed solvent is a mixed solvent of an alcohol and water, the alcohol solvent is preferably isopropanol, and the mixed solvent of an alcohol and water is preferably a mixed solvent of isopropanol and water; and (2) adding the compound of formula (I") to a solvent or a mixed solvent, followed by pulping, filtration and drying to obtain the desired crystal form A; wherein the solvent is an alcohol solvent, the mixed solvent is a mixed solvent of an alcohol and water, the alcohol solvent is preferably isopropanol, and the mixed solvent of an alcohol and water is preferably a mixed solvent of isopropanol and water.

The present invention also relates to a pharmaceutical composition comprising a salt, the crystal forms I and II of the compound of formula (I), the crystal forms 1, 2 and 3 of the compound of formula (I'), or the crystal form A of the compound of formula (I") and a pharmaceutically acceptable carrier.

The present invention further relates to use of the salt, the crystal forms I and II of the compound of formula (I), the crystal forms 1, 2 and 3 of the compound of formula (I'), the crystal form A of the compound of formula (I") or the pharmaceutical composition in the preparation of a medicament for the treatment or prevention of a disease related to renal outer medullary potassium channel (ROMK) inhibition.

The disease of the present invention is selected from the group consisting of hypertension and heart failure.

The research results show that crystal form I of the compound of formula (I) prepared according to the present invention is stable under conditions of lighting, high temperature and high humidity. Crystal form I is also stable under conditions of grinding, pressure and heating, which meets the medical needs of production, transportation and storage.

DETAILED DESCRIPTION OF THE INVENTION

Figure 1:
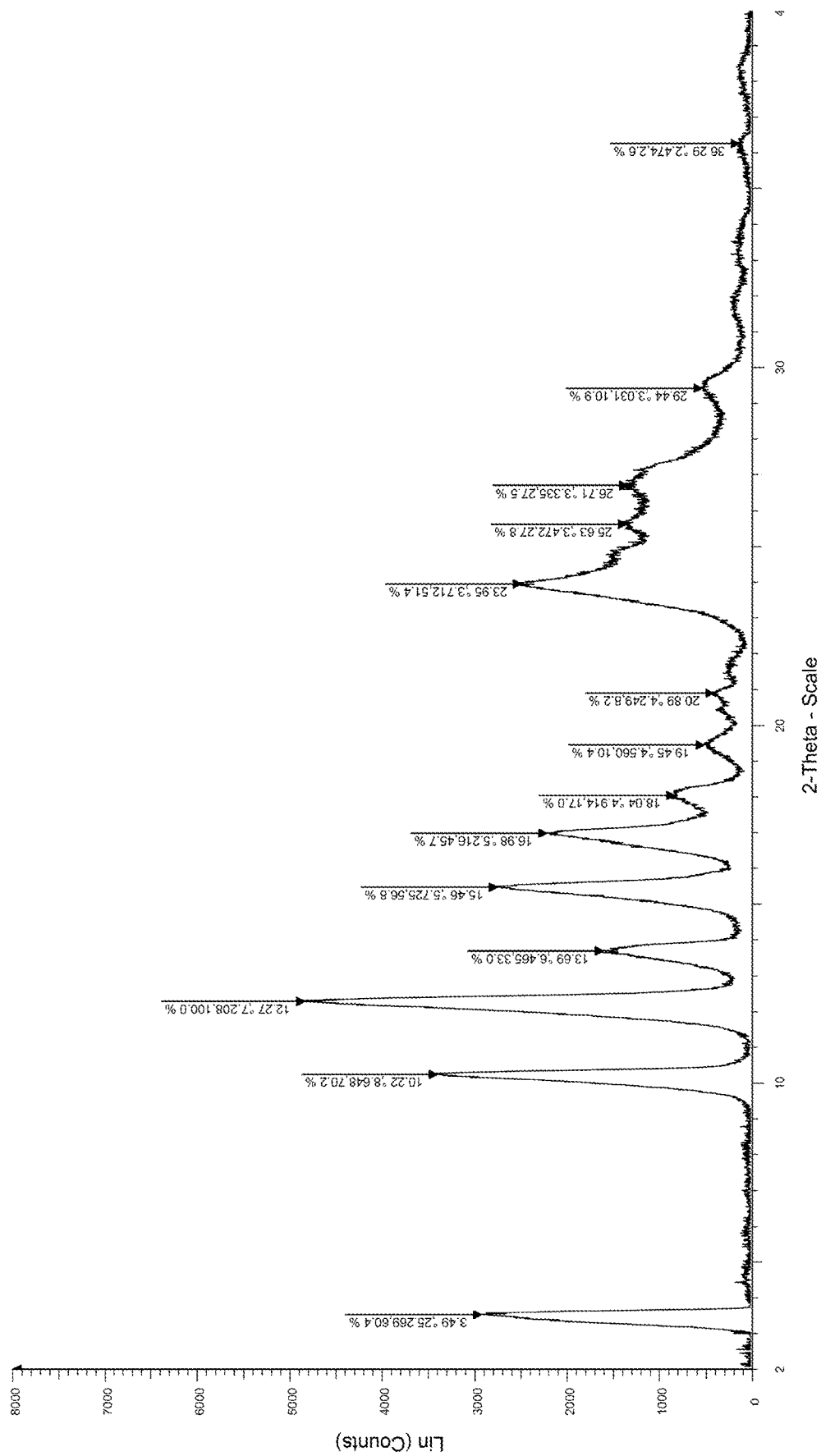
FIG. 1 shows the XRPD (X-ray powder diffraction) spectrum of crystal form I of the compound of formula (I).

The present invention is illustrated by the following examples in detail. The examples of the present invention are merely intended to describe the technical solution of the present invention, and should not be considered as limiting the scope of the present invention.

Testing instruments used in the experiments

1. DSC spectrum

Instrument type: Mettler Toledo DSC 1 Staree System

Purging gas: Nitrogen

Heating rate: 10.0° C./min

Temperature range: 40-350° C.

2. X-ray diffraction spectrum

Instrument type: Bruker D8 Focus X-ray powder diffractometer

Ray: monochromatic Cu-Kα ray ($\lambda=1.5406$)

Scanning mode: θ/2θ, Scanning range: 2-40°

Voltage: 40 KV, Electric current: 40 mA

Example 1

Synthesis of (R)-5-cyano-N-(1-(2-hydroxy-2-(4-methyl-1-oxo-1,3-dihydroisobenzofuran-5-yl)ethyl)piperidin-4-yl)-4-methoxypicolinamide

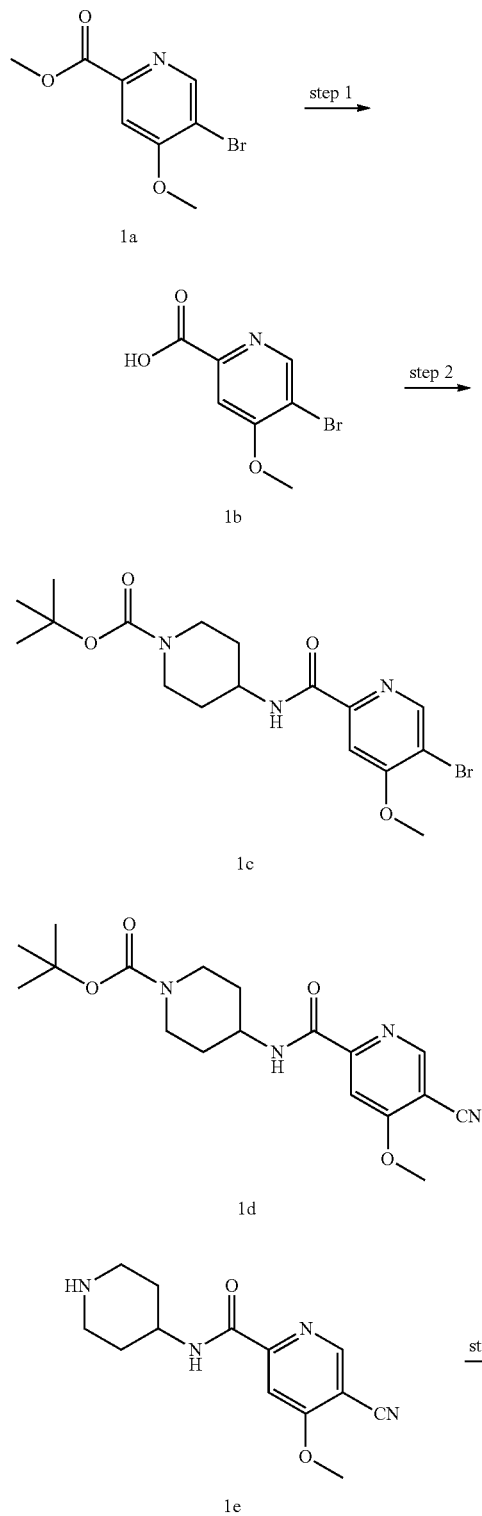

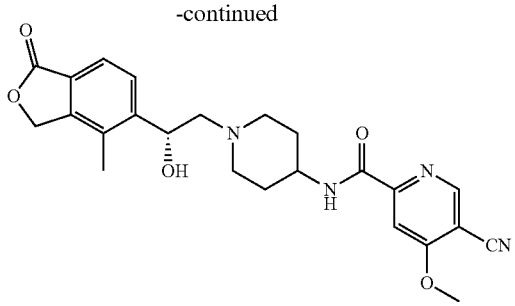

Step 1

5-Bromo-4-methoxypicolinic acid

Methyl 5-bromo-4-methoxypicolinate 1a (250 mg, 1.01 mmol) was dissolved in 10 mL of a mixed solvent of methanol, tetrahydrofuran and water (V:V:V=3:3:1), sodium hydroxide (100 mg, 2.5 mmol) was added and the mixture was stirred for 2 hours. The reaction solution was concentrated under reduced pressure, and 10 mL of water was added. The reaction solution was adjusted to pH 2 by adding 2M hydrochloric acid dropwise and extracted with ethyl acetate (20 mL×3). The organic phase was washed with saturated NaCl solution (15 mL×2), dried over anhydrous sodium sulfate, and filtered. The filtrate was concentrated under reduced pressure to obtain the crude title compound 5-bromo-4-methoxypicolinic acid 1b (200 mg, a white solid), which was used in the next step without further purification.

MS m/z (ESI): [M−1]$^+$=229.9.

Step 2 tert-Butyl 4-(5-bromo-4-methoxypicolinamido)piperidine-1-carboxylate

Crude 5-bromo-4-methoxypicolinic acid 1b (150 mg, 0.65 mmol), tert-butyl 4-aminopiperidine-1-carboxylate (130 mg, 0.65 mmol), 1-ethyl-(3-dimethylaminopropyl)carbodiimide (190 mg, 1 mmol), 1-hydroxybenzotriazole (20 mg, 0.13 mmol) and triethylamine (0.15 mL, 1 mmol) were dissolved in 20 mL of N,N-dimethylformamide. The reaction mixture was warmed up to 50° C. and stirred for 6 hours. The reaction solution was concentrated under reduced pressure. The resulting residue was purified by thin layer chromatography with n-hexane and ethyl acetate as the developing solvents to obtain the title compound tert-butyl 4-(5-bromo-4-methoxypicolinamido)piperidine-1-carboxylate 1c (60 mg, a light yellow oil), yield: 22.4%.

MS m/z (ESI): [M+1]$^+$=414.1.

Step 3 tert-Butyl 4-(5-cyano-4-methoxypicolinamido)piperidine-1-carboxylate tert-Butyl 4-(5-bromo-4-methoxypicolinamido)piperidine-1-carboxylate 1c (60 mg, 0.15 mmol), zinc cyanide (26 mg, 0.22 mmol) and tetra(phenylphosphine)palladium (18 mg, 0.015 mmol) were dissolved in 1.5 mL of N,N-dimethylacetamide. The reaction was carried out under microwave for 40 minutes at 135° C. The reaction solution was concentrated under reduced pressure. The resulting residue was purified by thin layer chromatography with n-hexane and ethyl acetate as the developing solvents to obtain the title compound tert-butyl 4-(5-cyano-4-methoxypicolinamido)piperidine-1-carboxylate 1d (32 mg, a colorless oil), yield: 61.5%.

MS m/z (ESI): [M+1]$^+$=361.2.

Step 4

5-Cyano-4-methoxy-N-(piperidin-4-yl)picolinamide tert-Butyl 4-(5-cyano-4-methoxypicolinamido)piperidine-1-carboxylate 1d (32 mg, 0.09 mmol) was dissolved in 5 mL of dichloromethane, and 1 mL of trifluoroacetic acid was added. The reaction mixture was stirred for 1.5 hours. The reaction solution was concentrated under reduced pressure, and 15 mL of methanol was added. The reaction solution was adjusted to pH 8 by adding saturated sodium bicarbonate solution dropwise, and then concentrated under reduced pressure. The resulting residue was purified by thin layer chromatography with dichloromethane and methanol as the developing solvents to obtain the title compound 5-cyano-4-methoxy-N-(piperidin-4-yl)picolinamide 1e (23 mg, a white paste), yield: 100%.

MS m/z (ESI): [M+1]$^+$=261.1.

Step 5

(R)-5-cyano-N-(1-(2-hydroxy-2-(4-methyl-1-oxo-1,3-dihydroisobenzofuran-5-yl)ethyl) piperidin-4-yl)-4-methoxypicolinamide (R)-4-methyl-5-(oxiran-2-yl)isobenzofuran-1(3H)-one (25 mg, 0.09 mmol, prepared according to the method disclosed in patent application "WO2010129379") and 5-cyano-4-methoxy-N-(piperidin-4-yl)picolinamide 1e (23 mg, 0.09 mmol) were dissolved in 5 mL of acetonitrile. The reaction mixture was stirred and heated to reflux for 15 hours. The reaction solution was concentrated under reduced pressure. The resulting residue was purified by thin layer chromatography with dichloromethane and methanol as the developing solvents to obtain the title compound (R)-5-cyano-N-(1-(2-hydroxy-2-(4-methyl-1-oxo-1,3-dihydroisobenzofuran-5-yl)ethyl) piperidin-4-yl)-4-methoxypicolinamide 1 (4.5 mg, a light yellow solid), yield: 11.3%.

MS m/z (ESI): [M+1]$^+$=450.2.

$^1$H NMR (400 MHz, d$_6$-DMSO): δ=8.88 (s, 1H), 8.75 (d, 1H), 7.77 (s, 1H), 7.71-7.69 (m, 2H), 5.43-5.40 (m, 2H), 5.35 (s, 1H), 5.08 (s, 1H), 4.09 (s, 3H), 3.78 (s, 1H), 2.95 (s, 3H), 2.38 (s, 1H), 2.27 (s, 3H), 2.25 (s, 2H), 1.72 (s, 4H) ppm.

Example 2. Preparation of Crystal Form I of the Tartrate

Figure 2:
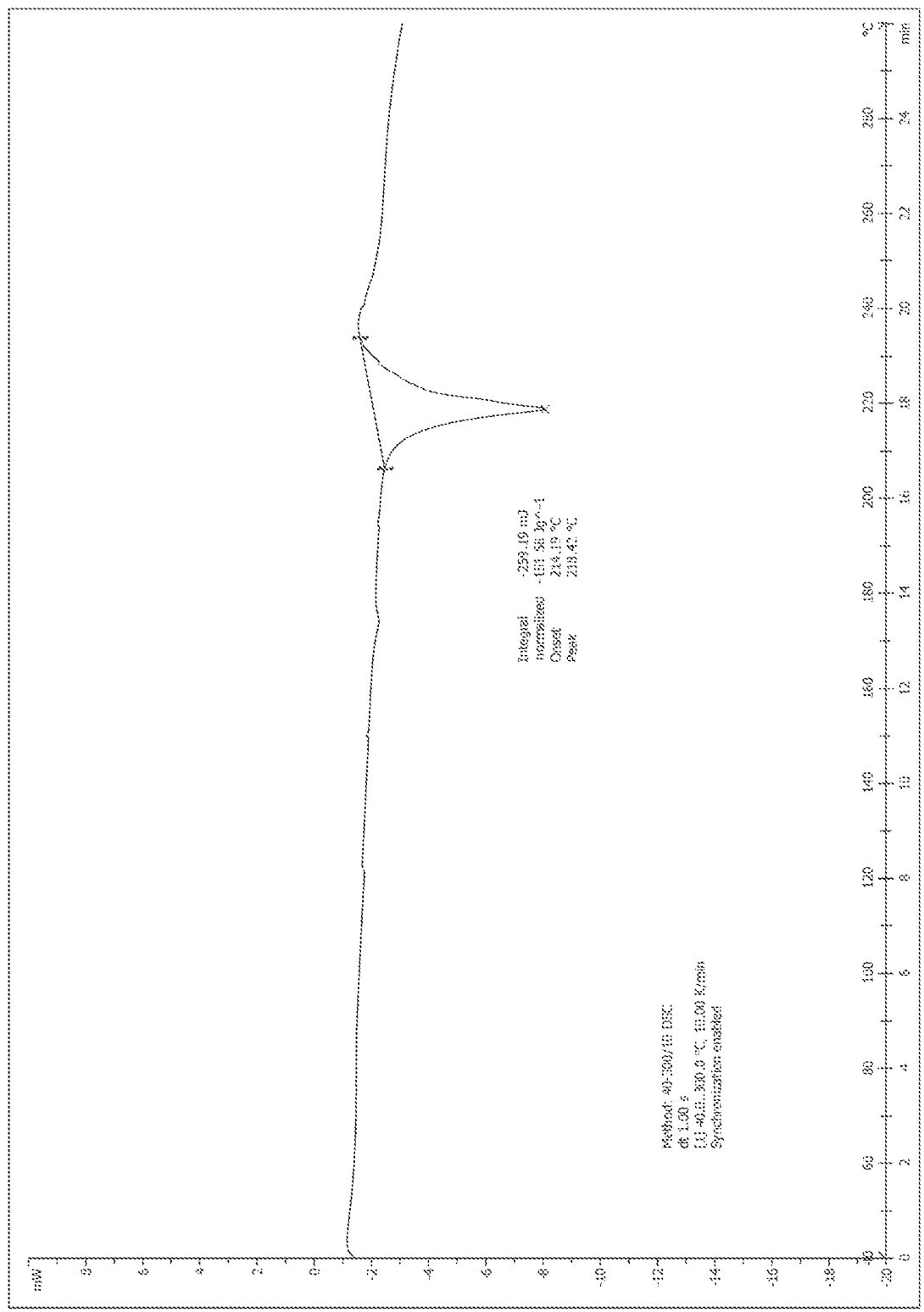
FIG. 2 shows the DSC spectrum of crystal form I of the compound of formula (I).

L-tartaric acid (0.4 g, 2.66 mmol) was added to a 50 ml reaction flask, 30 ml of methanol was added, and then the mixture was heated to 70° C. to dissolve. (R)-5-cyano-N-(1-(2-hydroxy-2-(4-methyl-1-oxo-1,3-dihydroisobenzofuran-5-yl)ethyl) piperidin-4-yl)-4-methoxypicolinamide (1.0 g, 2.22 mmol) (prepared according to the method of Example 1) was added, and then the reaction was carried out at 70° C. for 24 hours. The mixture was cooled to room temperature, filtered and dried to obtain 1.22 g of a solid, yield: 91.7%. The X-ray diffraction spectrum of the crystal sample is shown in FIG. 1. There are characteristic peaks at about 3.49(25.27), 10.22(8.65), 12.27(7.21), 13.69(6.47), 15.46(5.73), 16.98(5.22), 18.04(4.91), 19.45(4.56), 20.89 (4.25), 23.95 (3.71), 25.63(3.47), 26.71(3.34), and 29.44 (3.03). The DSC spectrum is shown in FIG. 2, having a sharp melting endothermic peak at 218.42° C. The crystal form was defined as crystal form I.

Figure 3:
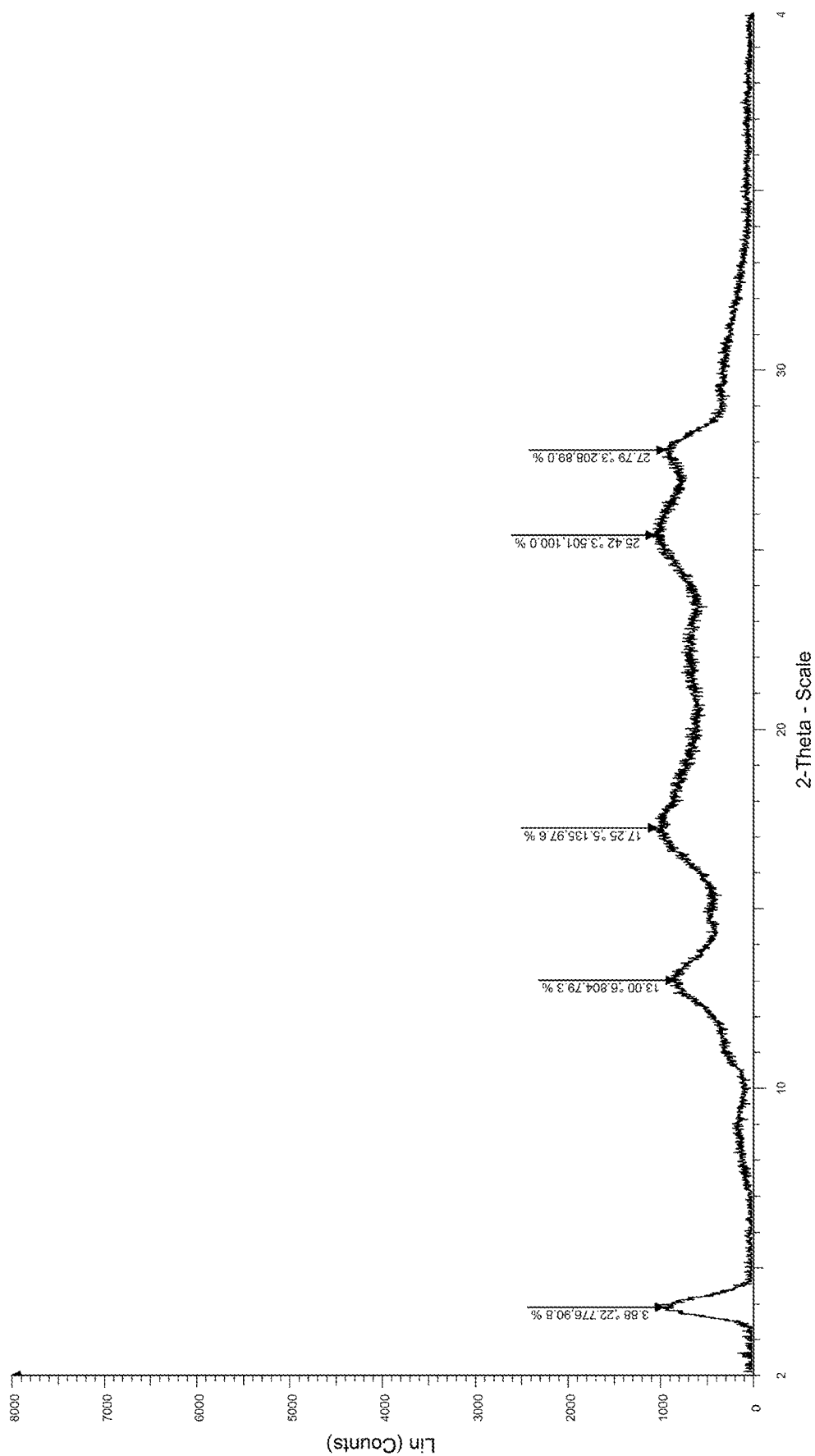
FIG. 3 shows the XRPD spectrum of crystal form II of the compound of formula (I).
Figure 4:
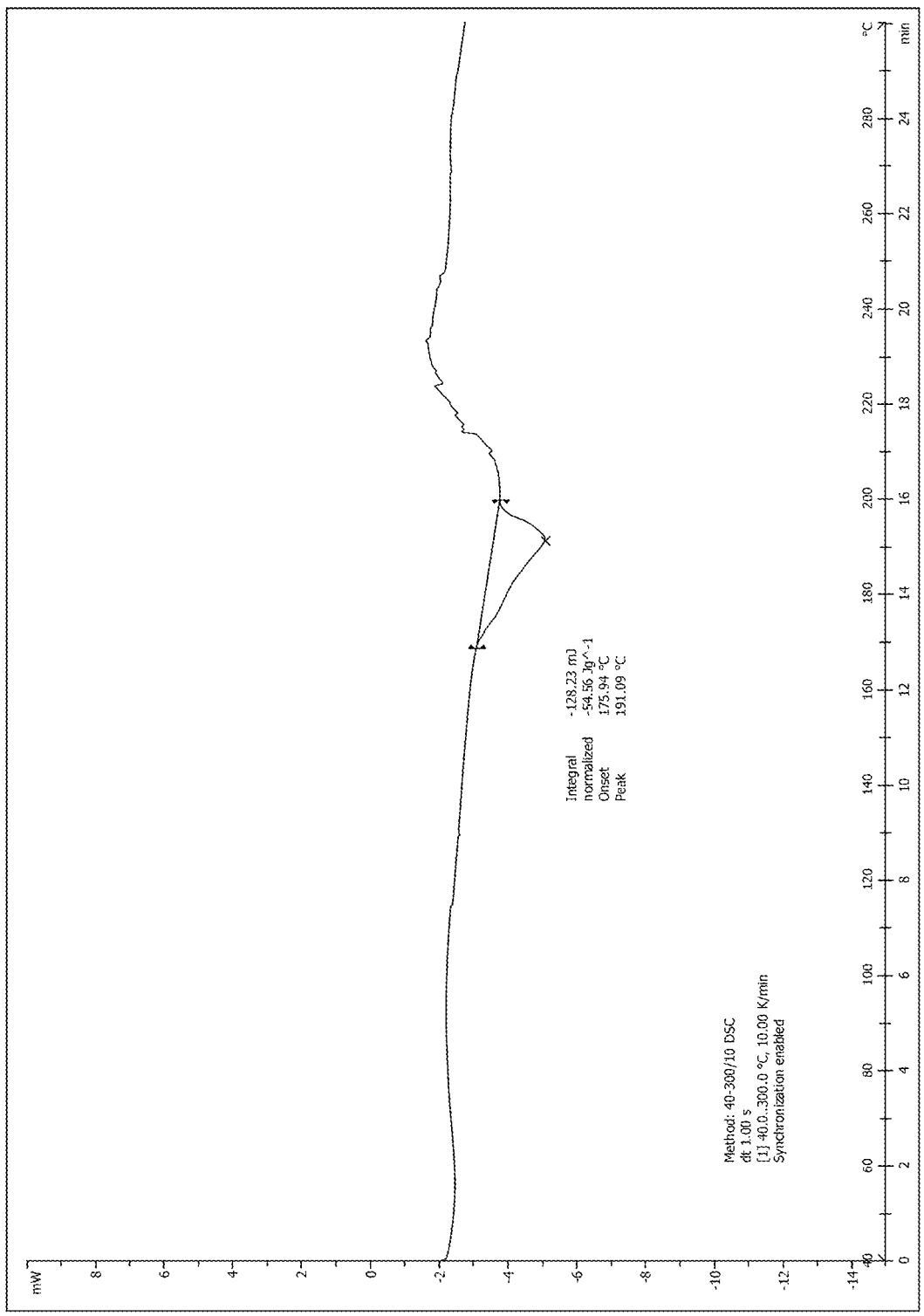
FIG. 4 shows the DSC spectrum of crystal form II of the compound of formula (I).

Example 3. Preparation of Crystal Form II of the Tartrate (R)-5-cyano-N-(1-(2-hydroxy-2-(4-methyl-1-oxo-1,3-dihydroisobenzofuran-5-yl)ethyl)piperidin-4-yl)-4-methoxypicolinamide (1.0 g, 2.22 mmol) (prepared according to the method of Example 1) and L-tartaric acid (0.4 g, 2.66 mmol) were added to a 50 ml reaction flask, 30 ml of isopropanol/tetrahydrofuran/water (V:V:V=20:10:1) was added, and the mixture was heated to 70° C. for 24 hours. The mixture was cooled to room temperature, filtered and dried to obtain 1.15 g of a solid, yield: 86.5%. The X-ray diffraction spectrum of the crystal sample is shown in FIG. 3. There are characteristic peaks at about 3.88(22.78), 13.00 (6.80), 17.25(5.14), 25.42(3.50), and 27.79(3.21). The DSC spectrum is shown in FIG. 4, having a wide melting endothermic peak at 191.09° C. The crystal form was defined as crystal form II.

Example 4. Preparation of Crystal Form I of the Tartrate

L-tartaric acid (0.4 g, 2.66 mmol) was added to a 50 ml reaction flask, 30 ml of ethanol/water (V:V=9:1) was added, and then the mixture was heated to 70° C. to dissolve. (R)-5-cyano-N-(1-(2-hydroxy-2-(4-methyl-1-oxo-1,3-dihydroisobenzofuran-5-yl)ethyl) piperidin-4-yl)-4-methoxypicolinamide (1.0 g, 2.22 mmol) (prepared according to the method of Example 1) was added, and then the reaction was carried out at 70° C. for 24 hours. The mixture was cooled to room temperature, filtered and dried to obtain 1.24 g of a solid, yield: 93.2%. The product was identified as crystal form I after studying and comparing the X-ray diffraction and DSC spectra.

Example 5. Preparation of Crystal Form I of the Tartrate

L-tartaric acid (0.4 g, 2.66 mmol) was added to a 50 ml reaction flask, 30 ml of ethanol/water (V:V=19:1) was added, and then the mixture was heated to 70° C. to dissolve. (R)-5-cyano-N-(1-(2-hydroxy-2-(4-methyl-1-oxo-1,3-dihydroisobenzofuran-5-yl)ethyl) piperidin-4-yl)-4-methoxypicolinamide (1.0 g, 2.22 mmol) (prepared according to the method of Example 1) was added, and then the reaction was carried out at 70° C. for 24 hours. The mixture was cooled to room temperature, filtered and dried to obtain 1.20 g of a solid, yield: 90.2%. The product was identified as crystal form I after studying and comparing the X-ray diffraction and DSC spectra.

Example 6. Preparation of the Maleate (R)-5-cyano-N-(1-(2-hydroxy-2-(4-methyl-1-oxo-1,3-dihydroisobenzofuran-5-yl)ethyl)piperidin-4-yl)-4-methoxypicolinamide (600 mg, 1.32 mmol) was added to 20 mL of ethanol. The mixture did not become clear after heating to 70° C. and stirring for 1 hour. The solution became clear rapidly after addition of maleic acid (186 mg, 1.6 mmol). The mixture was stirred at 70° C. for 18 hours, and a small amount of solid was precipitated. The mixture was cooled naturally to room temperature, and a large amount of solid was precipitated after 2 hours. The reaction solution was filtered. The filter cake was rinsed with ethanol (2 mL×2), collected and dried in a vacuum to obtain the title compound (600 mg, a white solid), yield: 79%.

The $^1$H-NMR nuclear magnetic data showed that the molar ratio of the main component to maleic acid in the salt was 1:1;

$^1$H-NMR (400 MHz, DMSO-d$_6$) δ 2.00 (d, 4H) 2.33 (br. s., 3H) 3.17 (br. s., 3H) 3.44 (br. s., 1H) 3.59 (br. s., 1H) 3.74 (br. s., 1H) 4.11 (s, 4H) 4.37 (br. s., 1H) 5.28-5.52 (m, 3H) 6.02 (s, 2H) 6.35 (br. s., 1H) 7.63-7.89 (m, 3H) 8.93 (s, 1H) 9.11 (br. s., 1H) 9.58 (br. s., 1H).

Example 7. Preparation of the Hydrochloride (R)-5-cyano-N-(1-(2-hydroxy-2-(4-methyl-1-oxo-1,3-dihydroisobenzofuran-5-yl)ethyl)piperidin-4-yl)-4-methoxypicolinamide (100 mg, 0.22 mmol) was dissolved in 3 mL of ethanol, but it was not fully dissolved after heating to 70° C. for 30 minutes. 12 M concentrated hydrochloric acid (0.02 mL, 0.29 mmol) was added dropwise to the above solution, and there was no significant change. The solution was heated to 70° C. and stirred for 17 hours, and then a white powder appeared in the solution. The reaction solution was filtered while it was still hot. The filter cake was washed with ethanol (2 mL×2), collected and dried in a vacuum to obtain the title compound (85 mg, a white solid), yield: 79%.

$^1$H-NMR (400 MHz, DMSO-d$_6$) δ 1.91-2.19 (m, 4H) 2.32-2.40 (m, 3H) 3.07-3.29 (m, 3H) 3.41-3.56 (m, 1H) 3.76 (br. s., 1H) 3.98-4.20 (m, 4H) 5.37-5.49 (m, 2H) 5.55 (d, 1H) 6.43 (d, 1H) 7.71-7.82 (m, 3H) 8.86-8.93 (m, 1H) 9.08 (d, 1H) 10.27 (br. s., 1H).

Example 8. Preparation of the Sulfate (R)-5-cyano-N-(1-(2-hydroxy-2-(4-methyl-1-oxo-1,3-dihydroisobenzofuran-5-yl)ethyl)piperidin-4-yl)-4-methoxypicolinamide (150 mg, 0.33 mmol) was dissolved in a mixed solution of 8 mL of dichloromethane and 4 mL of isopropanol, but it was not fully dissolved. Concentrated sulfuric acid (42 mg, 0.43 mmol) was added dropwise to the above solution, which was stirred at room temperature (16° C.) for 4 hours, and then 4 mL of methyl tert-butyl ether were added. The reaction solution was cooled in an ice bath to precipitate a solid, and then filtered. The filter cake was collected and dried in a vacuum to obtain the title compound (153 mg, a white solid), yield: 85%.

$^1$H-NMR (400 MHz, DMSO-d$_6$) δ 1.89-2.18 (m, 4H), 2.30-2.40 (m, 3H), 3.07-3.30 (m, 3H), 3.45 (br. s., 1H), 3.66 (d, 1H), 3.75-3.85 (m, 1H), 3.97-4.19 (m, 3H), 5.31-5.53 (m, 3H), 6.28-6.48 (m, 1H), 7.71-7.83 (m, 3H), 8.83-8.96 (m, 1H), 9.10 (d, 1H), 9.51 (br. s., 1H).

Example 9. Preparation of the Citrate (R)-5-cyano-N-(1-(2-hydroxy-2-(4-methyl-1-oxo-1,3-dihydroisobenzofuran-5-yl)ethyl)piperidin-4-yl)-4-methoxypicolinamide (161 mg, 0.36 mmol) was dissolved in 5 mL of isopropanol, but it was not fully dissolved. Citric acid (89 mg, 0.46 mmol) was added to the above solution. The materials were not fully dissolved after heating to reflux and stirring for 16 hours, and there were massive and powdery solids. The mixture was filtered, and the filter cake was collected and dried in a vacuum. The solid was crushed and mixed well to obtain the title compound (150 mg, a white solid), yield: 65%.

The $^1$H-NMR nuclear magnetic data showed that the molar ratio of the main component to citric acid in the salt was 1:1.

$^1$H-NMR (400 MHz, DMSO-d$_6$) δ 1.83 (br. s., 4H), 2.30 (s, 3H), 2.52-2.65 (m, 3H), 2.67 (br. s., 1H), 2.70-2.82 (m, 2H), 3.21 (br. s., 2H), 3.32 (br. s., 1H), 3.69-3.82 (m, 1H), 3.92 (br. s., 1H), 4.10 (s, 3H), 4.34 (br. s., 1H), 5.19 (d, 1H), 5.35-5.47 (m, 2H), 7.68-7.74 (m, 2H), 7.78 (s, 1H), 8.85 (d, 1H), 8.90 (s, 1H).

Example 10. Preparation of the Phosphate (R)-5-cyano-N-(1-(2-hydroxy-2-(4-methyl-1-oxo-1,3-dihydroisobenzofuran-5-yl)ethyl)piperidin-4-yl)-4-methoxypicolinamide (100 mg, 0.22 mmol) was dissolved in 3 mL of isopropanol, but it was not fully dissolved after heating to 70° C. for 30 minutes. Phosphoric acid (33 mg, 0.29 mmol) was added dropwise to the above solution, and then a solid was condensed and precipitated in the solution. The mixture was heated to 70° C. and stirred for 16 hours, and the solid in the solution was powdery. The mixture was filtered without cooling, and the filter cake was collected and washed with isopropanol (2 mL×2) to obtain the title compound (110 mg, a white solid), yield: 91%.

$^1$H-NMR (400 MHz, DMSO-d$_6$) δ 1.82 (br. s., 4H), 2.29 (s, 3H), 2.50-2.78 (m, 4H), 3.18 (br. s., 2H), 3.88 (br. s., 1H), 4.03-4.16 (m, 3H), 5.19 (d, 1H), 5.34-5.46 (m, 2H), 7.68-7.74 (m, 2H), 7.78 (s, 1H), 8.82 (d, 1H), 8.90 (s, 1H).

Example 11. Preparation of the Fumarate

Method 1. (R)-5-cyano-N-(1-(2-hydroxy-2-(4-methyl-1-oxo-1,3-dihydroisobenzofuran-5-yl)ethyl) piperidin-4-yl)-4-methoxypicolinamide (152 mg, 0.38 mmol) was dissolved in a mixed solution of 6 mL of dichloromethane and 3 mL of methanol. Fumaric acid (51 mg, 0.44 mmol) was dissolved in 1.5 mL of ethanol, and then added dropwise to the above solution. The solution was heated to 40° C. and stirred for 18 hours, then cooled in an ice bath, and no solid was precipitated. 6 mL of methyl tert-butyl ether was added to the reaction solution, and still no solid was precipitated. Another 6 mL of methyl tert-butyl ether was added, leading to a solid precipitate. The mixture was filtered under reduced pressure to obtain the title compound (165 mg, a white solid), yield: 77%;

The $^1$H-NMR nuclear magnetic data showed that the molar ratio of the main component to fumaric acid in the salt was 1:0.5;

$^1$H-NMR (400 MHz, DMSO-d$_6$) δ 1.64-1.80 (m, 4H), 2.20-2.36 (m, 6H), 2.41-2.48 (m, 1H), 2.52-2.60 (m, 1H), 3.00 (d, 2H), 3.17 (s, 1H), 3.80 (br. s., 1H), 4.10 (s, 3H), 5.10 (dd, 1H), 5.34-5.45 (m, 2H), 6.59 (s, 1H), 7.65-7.72 (m, 2H), 7.78 (s, 1H), 8.76 (d, 1H), 8.89 (s, 1H).

Method 2. (R)-5-cyano-N-(1-(2-hydroxy-2-(4-methyl-1-oxo-1,3-dihydroisobenzofuran-5-yl)ethyl) piperidin-4-yl)-4-methoxypicolinamide (100 mg, 0.22 mmol) and fumaric acid (31 mg, 0.26 mmol) were dissolved in a mixed solution of 1 mL of dioxane and 0.5 mL of acetonitrile. The reaction solution became clear after heating to 70° C. and stirring for 18 hours. A solid was precipitated after the reaction solution was cooled to room temperature (20° C.). The mixture was filtered under reduced pressure to obtain the title compound (70 mg, a white solid), yield: 56%.

The $^1$H-NMR nuclear magnetic data showed that the molar ratio of the main component to fumaric acid in the salt was 1:1.

$^1$H-NMR (400 MHz, DMSO-d$_6$) δ 1.76 (br. s., 4H), 2.25-2.38 (m, 6H), 2.54-2.62 (m, 1H), 3.04 (d, 2H) 3.81 (br. s., 1H), 4.10 (s, 3H), 5.12 (dd, 1H), 5.34-5.47 (m, 2H), 6.60 (s, 2H), 7.64-7.74 (m, 2H), 7.78 (s, 1H), 8.77 (d, 1H), 8.89 (s, 1H).

Example 12. Preparation of the Succinate (R)-5-cyano-N-(1-(2-hydroxy-2-(4-methyl-1-oxo-1,3-dihydroisobenzofuran-5-yl)ethyl)piperidin-4-yl)-4-methoxypicolinamide (50 mg, 0.11 mmol) and succinic acid (15 mg, 0.13 mmol) were dissolved in 1.5 mL of methanol. The materials were not fully dissolved after heating to 60° C. for 4 hours. The mixture was cooled naturally to room temperature (19° C.) and stirred for 18 hours, and then filtered. The filter cake was washed with 1 mL of methanol, and dried to obtain the title compound (50 mg, a white solid), yield: 81%.

Example 13. Preparation of Crystal Form 1 of the Malate (R)-5-cyano-N-(1-(2-hydroxy-2-(4-methyl-1-oxo-1,3-dihydroisobenzofuran-5-yl)ethyl)piperidin-4-yl)-4-methoxypicolinamide (50 mg, 0.11 mmol) was added to a mixed solution of 1.5 mL of methanol and 0.15 mL of water, and then malic acid (17 mg, 0.13 mmol) was added. The mixture did not become clear after heating to 50° C. and stirring for 4 hours. The mixture was cooled naturally to room temperature and stirred for 16 hours. The reaction solution was filtered, and the filter cake was rinsed with ethanol (5 mL×2), collected and dried in a vacuum to obtain the title compound (40 mg, a white solid), yield: 67%.

Figure 5:
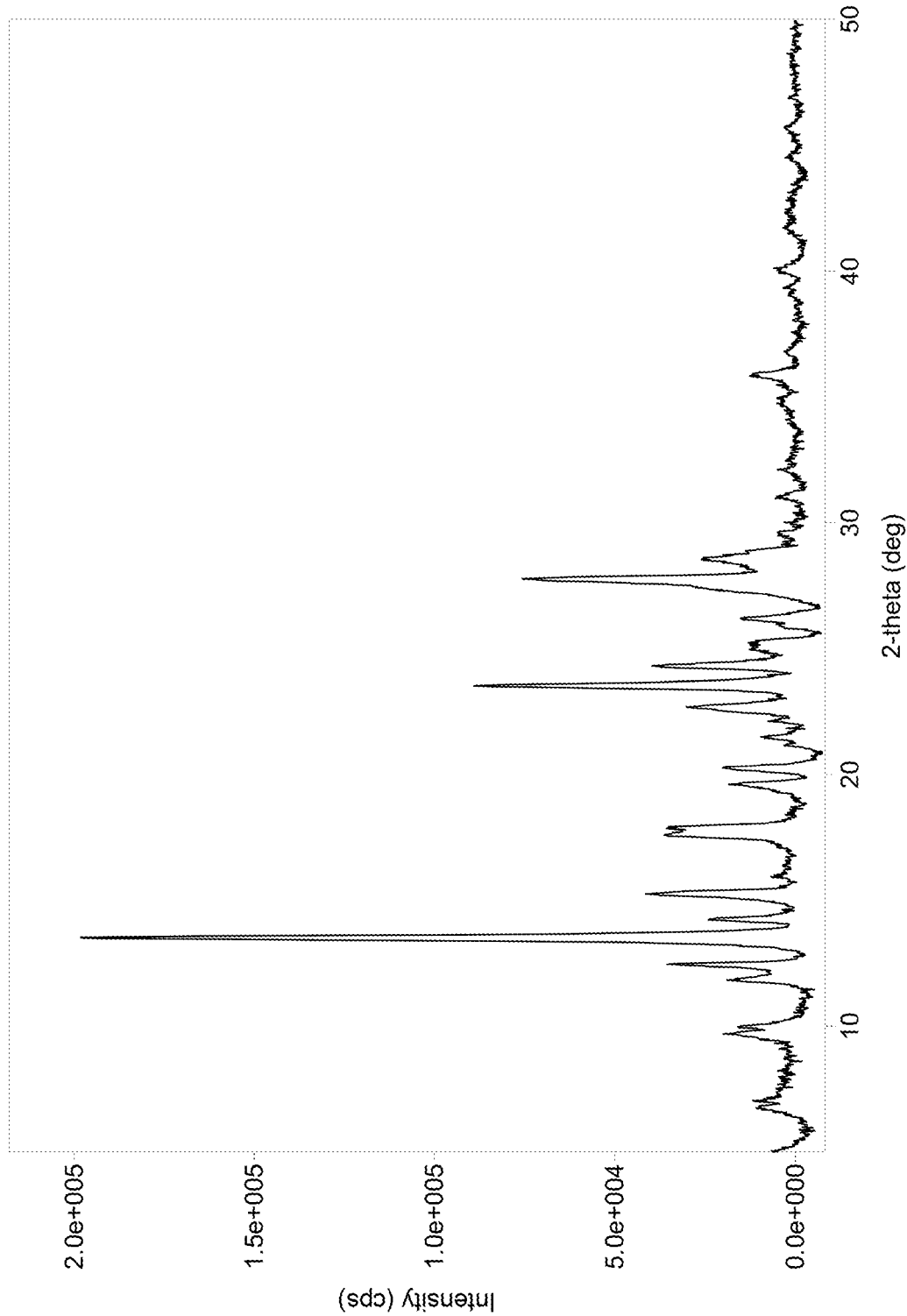
FIG. 5 shows the XRPD spectrum of crystal form 1 of the compound of formula (I').
Figure 6:
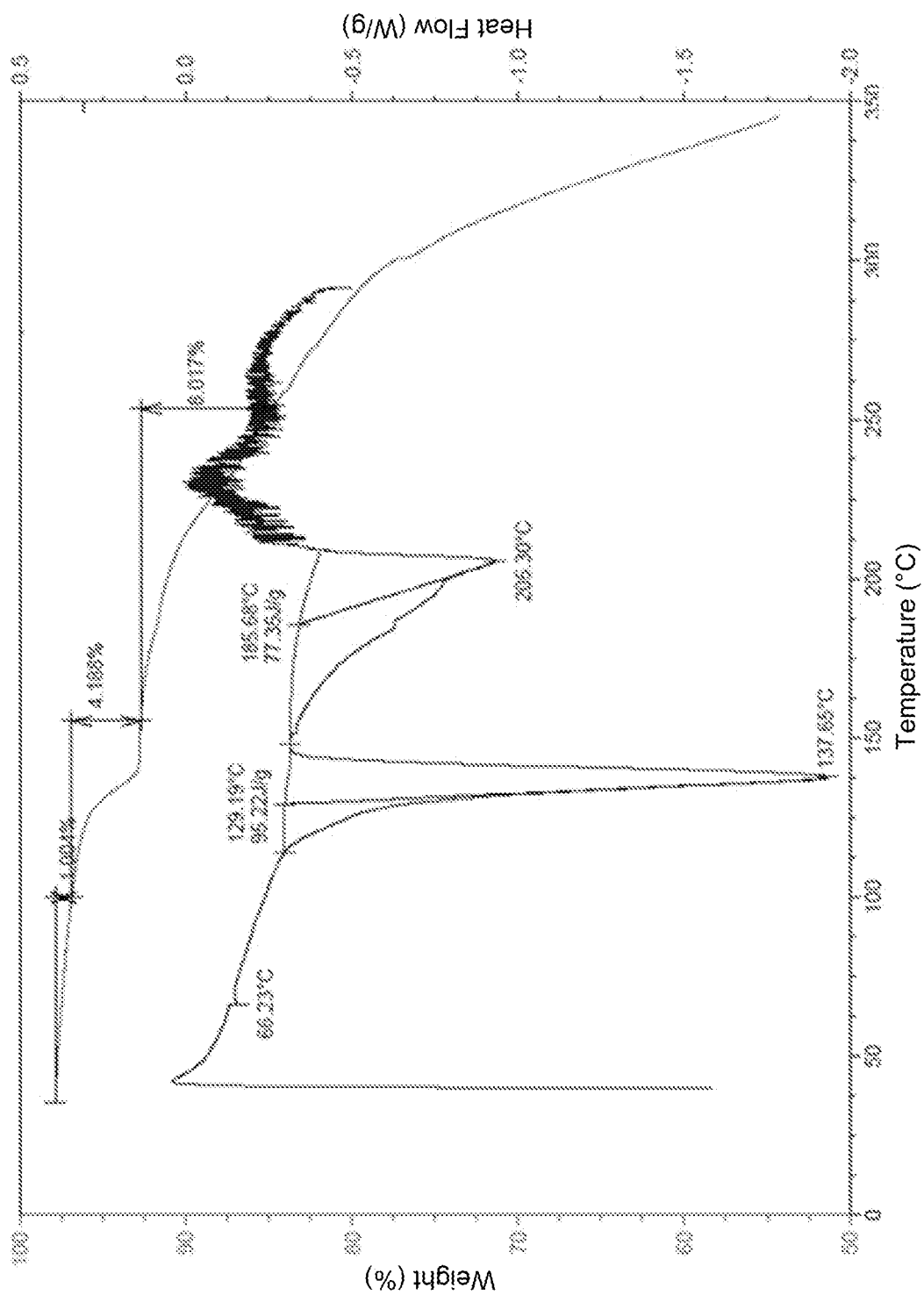
FIG. 6 shows the DSC-TGA spectrum of crystal form 1 of the compound of formula (I').

The sample has characteristic peaks at 6.85(12.9), 9.76 (9.06), 11.81(7.49), 12.48(7.09), 13.52(6.54), 14.23(6.22), 15.29(5.79), 15.94(5.56), 17.55(5.05), 17.89(4.96), 19.65 (4.51), 20.25(4.38), 21.50(4.13), 22.68(3.92), 23.50(3.78), 24.27(3.66), 25.22(3.53), 26.18(3.40), 27.83(3.20), 28.59 (3.12), 34.88(2.57), and 35.84(2.50). The X-ray powder diffraction spectrum (XRPD spectrum) thereof is shown in FIG. 5. The DSC-TGA spectrum is shown in FIG. 6, having a sharp melting endothermic peak at 137.65° C. The crystal form was defined as crystal form 1.

Example 14. Preparation of Crystal Form 2 of the Malate (R)-5-cyano-N-(1-(2-hydroxy-2-(4-methyl-1-oxo-1,3-dihydroisobenzofuran-5-yl)ethyl)piperidin-4-yl)-4-methoxypicolinamide (50 mg, 0.11 mmol) was added to a mixed solution of 1.5 mL of acetonitrile and 0.15 mL of deionized water, and then malic acid (17 mg, 0.13 mmol) was added. The mixture became clear after heating to 50° C. and stirring for 4 hours. The mixture was cooled naturally to room temperature and stirred for 16 hours to precipitate a solid. The reaction solution was filtered, and the filter cake was collected and dried in a vacuum to obtain the title compound (40 mg, a white solid), yield: 67%.

The $^1$H-NMR nuclear magnetic data showed that the molar ratio of the main component to malic acid in the salt was 1:1.

$^1$H-NMR (400 MHz, DMSO-d$_6$) δ 1.67-1.91 (m, 4H), 2.29 (s, 3H), 2.39-2.44 (m, 2H), 2.57 (dd, 2H), 2.62-2.77 (m, 2H), 3.10-3.23 (m, 2H), 3.83-3.95 (m, 1H), 4.04-4.17 (m, 4H), 5.18 (dd, 1H), 5.33-5.49 (m, 2H), 7.67-7.74 (m, 2H), 7.78 (s, 1H), 8.83 (d, 1H), 8.90 (s, 1H).

Figure 7:
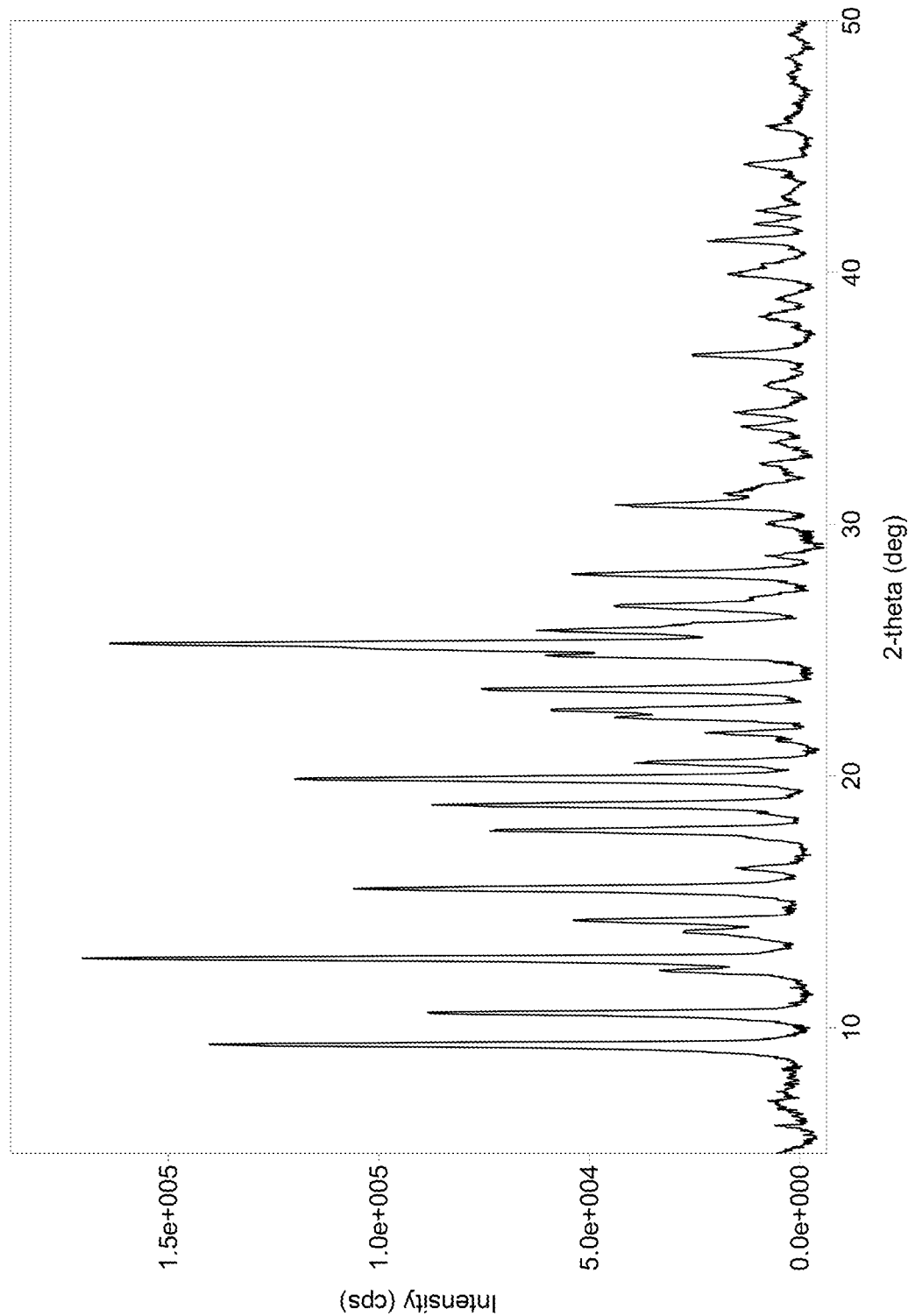
FIG. 7 shows the XRPD spectrum of crystal form 2 of the compound of formula (I').
Figure 8:
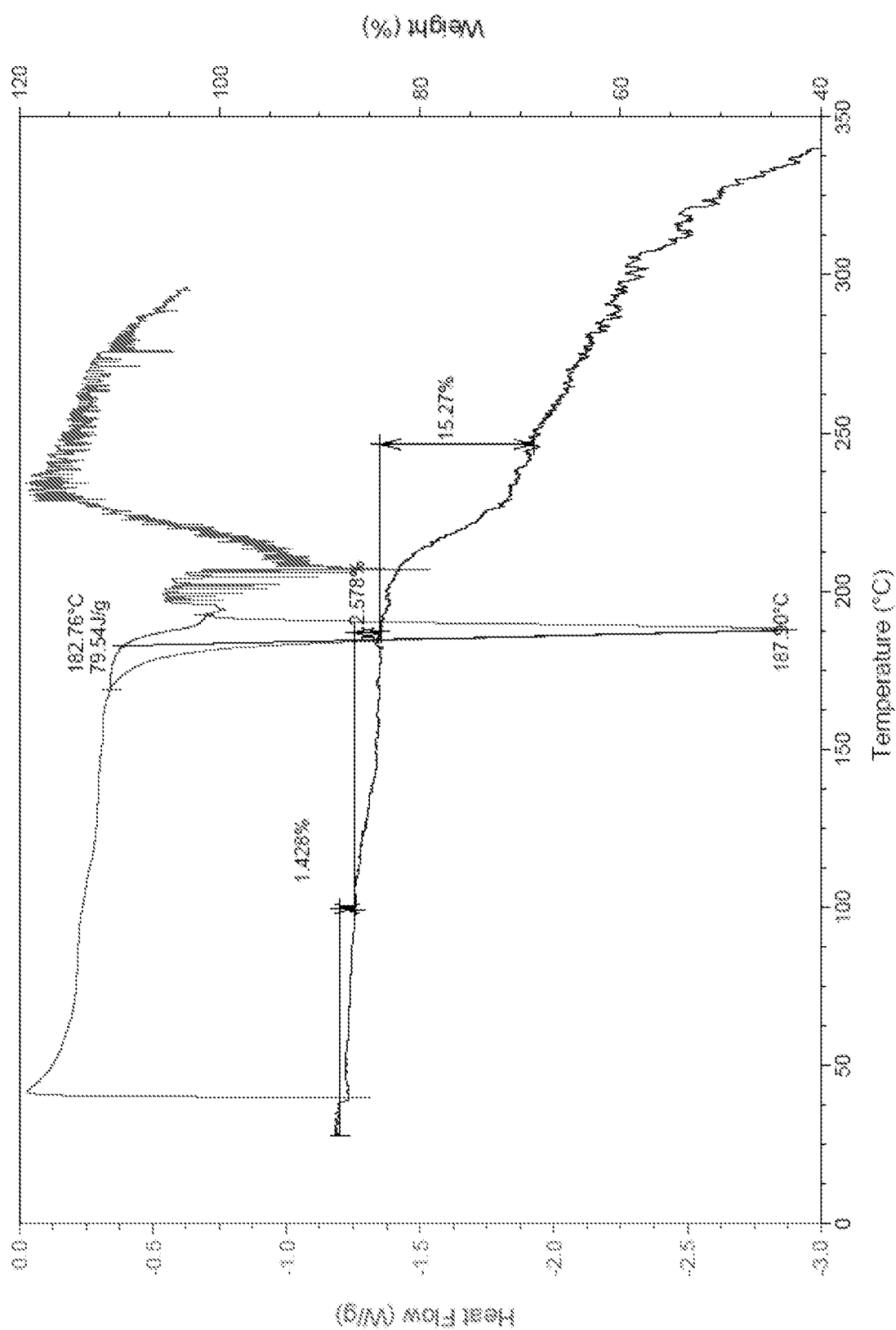
FIG. 8 shows the DSC-TGA spectrum of crystal form 2 of the compound of formula (I').

The sample has characteristic peaks at 7.30(12.00), 9.34 (9.46), 10.61(8.33), 12.24(7.23), 12.78(6.92), 13.83(6.40), 14.26(6.21), 15.52(5.71), 16.33(5.42), 17.83(4.97), 18.83 (4.71), 19.86(4.47), 20.55(4.32), 21.72(4.09), 22.31(3.98), 22.62(3.93), 23.42(3.80), 24.78(3.59), 25.03(3.55), 25.27 (3.52), 25.78(3.45), 26.02(3.42), 26.76(3.33), 27.10(3.29), 27.99(3.19), 30.01(2.98), 30.72(2.91), 31.19(2.87), 32.41 (2.76), 33.23(2.69), 33.83(2.65), 34.41(2.60), 35.48(2.53), 36.68(2.45), 38.20(2.35), 38.92(2.31), 39.87(2.26), 41.25 (2.19), 41.94(2.15), 42.38(2.13), 44.25(2.05), and 45.72 (1.98). The X-ray powder diffraction spectrum (XRPD spectrum) thereof is shown in FIG. 7. The DSC-TGA spectrum is shown in FIG. 8, having a sharp melting endothermic peak at 187.90° C. The crystal form was defined as crystal form 2.

Figure 9:
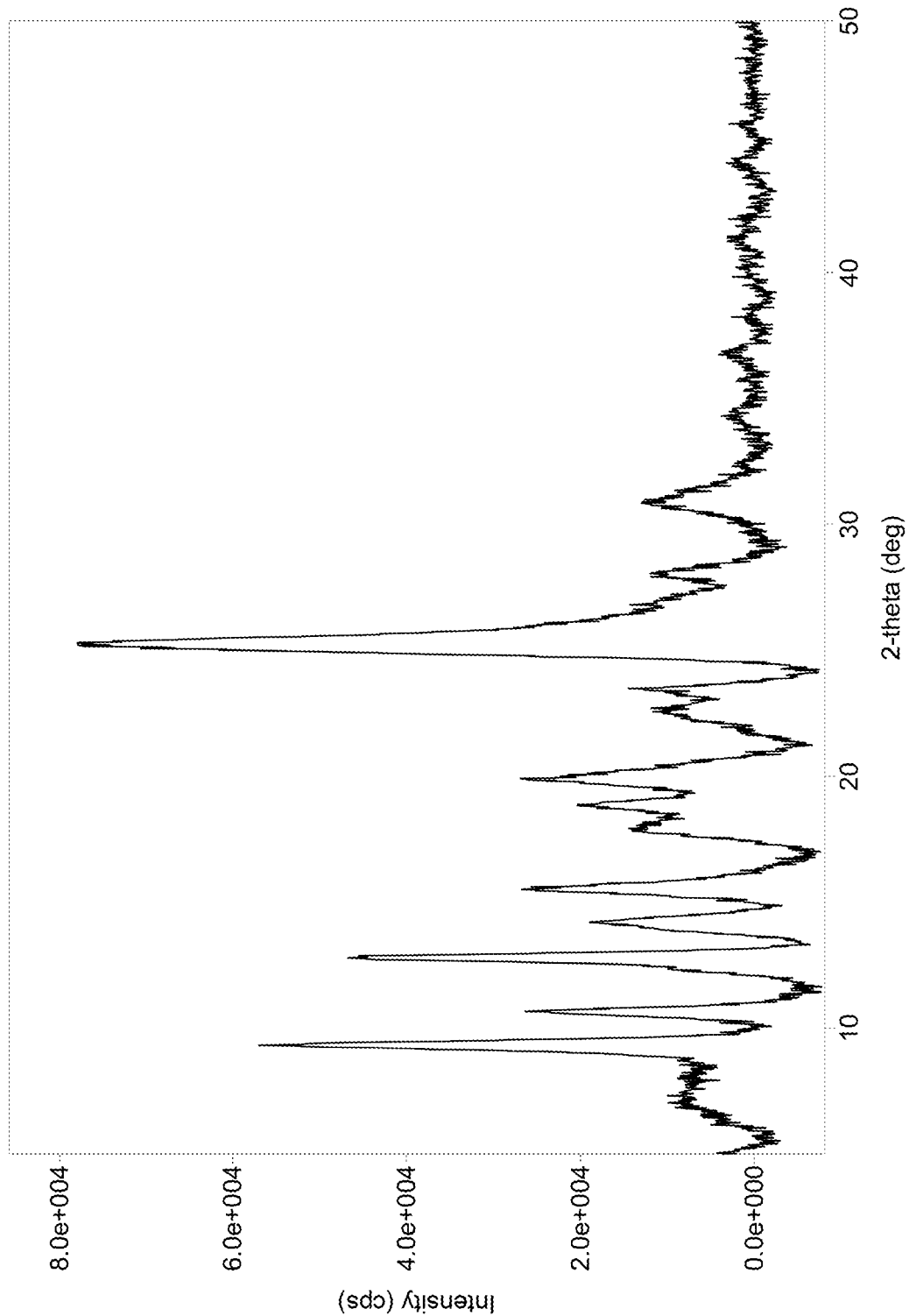
FIG. 9 shows the XRPD spectrum of crystal form 3 of the compound of formula (I').

Example 15. Preparation of Crystal Form 3 of the Malate (R)-5-cyano-N-(1-(2-hydroxy-2-(4-methyl-1-oxo-1,3-dihydroisobenzofuran-5-yl)ethyl)piperidin-4-yl)-4-methoxypicolinamide (50 mg, 0.11 mmol) was added to 1.5 mL of isopropanol, and then malic acid (17 mg, 0.13 mmol) was added. The mixture did not become clear after heating to 60° C. and stirring for 4 hours. The mixture was cooled naturally to room temperature and stirred for 16 hours to precipitate a colloidal solid. The reaction solution was filtered, and the filter cake was rinsed with isopropanol (1 mL×1), collected and dried in a vacuum to obtain the title compound (50 mg, a white solid), yield: 80%;

The sample has characteristic peaks at 7.07(12.49), 9.34 (9.47), 10.63(8.31), 12.79(9.92), 14.22(6.22), 15.50(5.71), 17.84(4.97), 18.86(4.70), 19.93(4.45), 22.56(3.94), 23.51 (3.78), 25.16(3.54), and 30.90(2.89). The X-ray powder diffraction spectrum (XRPD spectrum) thereof is shown in FIG. 9. The crystal form was defined as crystal form 3.

Example 16. Preparation of Crystal Form A of the Malate (R)-5-cyano-N-(1-(2-hydroxy-2-(4-methyl-1-oxo-1,3-dihydroisobenzofuran-5-yl)ethyl)piperidin-4-yl)-4-methoxypicolinamide (50 mg, 0.11 mmol) was added to a mixed solution of 1.5 mL of isopropanol and 0.15 mL of water, and then malic acid (17 mg, 0.13 mmol) was added. The mixture did not become clear after heating to 50° C. and stirring for 4 hours. The mixture was cooled naturally to room temperature and stirred for 16 hours. The reaction solution was filtered, and the filter cake was rinsed with ethanol (5 mL×2), collected and dried in a vacuum to obtain the title compound (40 mg, a white solid), yield: 67%.

The $^1$H-NMR nuclear magnetic data showed that the molar ratio of the main component to malic acid in the salt was 1:0.5.

$^1$H-NMR (400 MHz, DMSO-d$_6$) δ 1.73 (br. s., 1H) 1.78 (br. s., 3H) 2.29 (s, 3H) 2.33-2.44 (m, 2H) 2.55 (dd, 2H) 2.60-2.68 (m, 1H) 3.09 (br. s., 2H) 3.86 (br. s., 1H) 4.00-4.16 (m, 4H) 5.14 (d, 1H) 5.33-5.46 (m, 2H) 7.66-7.74 (m, 2H) 7.78 (s, 1H) 8.80 (d, 1H) 8.89 (s, 1H).

Figure 10:
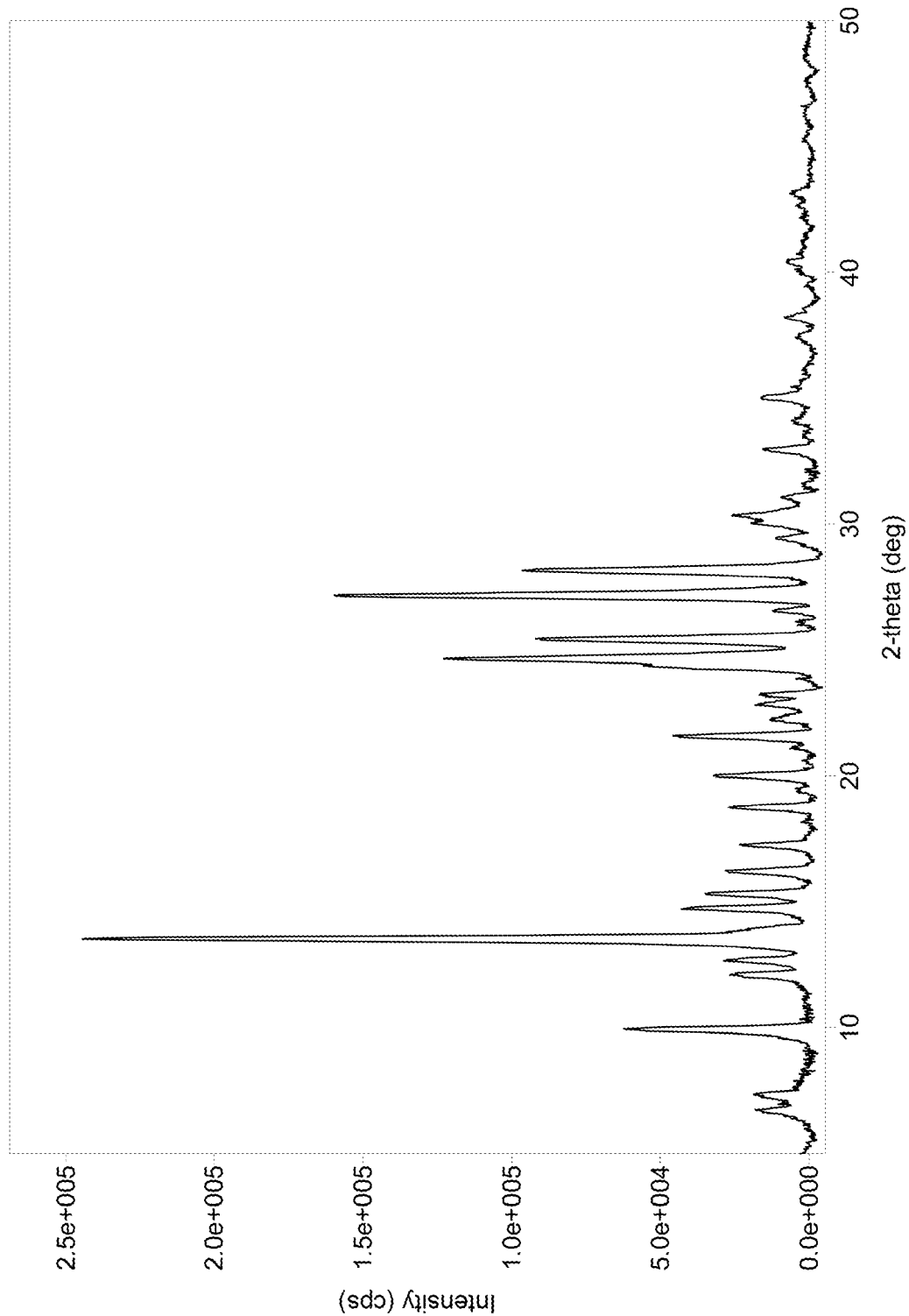
FIG. 10 shows the XRPD spectrum of crystal form A of the compound of formula (I").
Figure 11:
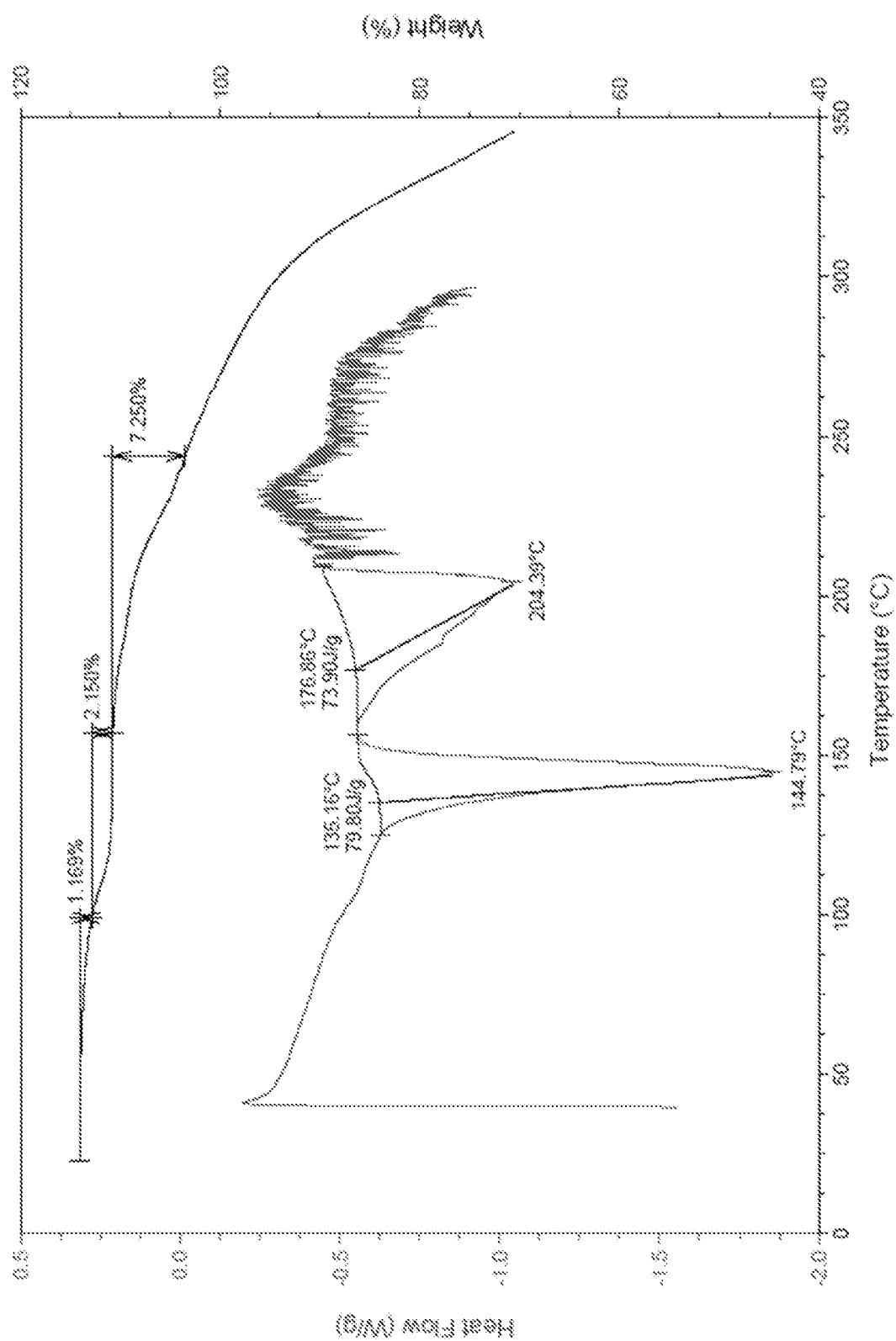
FIG. 11 shows the DSC-TGA spectrum of crystal form A of the compound of formula (I").

The sample has characteristic peaks at 7.36(12.00), 9.95 (8.88), 12.12(7.30), 12.68(6.97), 13.56(6.53), 14.73(6.01), 15.32(5.78), 16.20(5.47), 17.27(5.13), 18.74(4.73), 20.00 (4.44), 21.57(4.12), 22.21(4.00), 22.82(3.89), 23.22(3.83), 24.35(3.65), 24.63(3.61), 25.42(3.50), 26.57(3.35), 27.13 (3.28), 28.15(3.17), 29.45(3.03), 30.01(2.98), 30.30(2.95), 31.09(2.87), 32.92(2.72), 34.01(2.63), 34.97(2.56), 38.17 (2.36), 40.33(2.24), and 43.19(2.09). The X-ray powder diffraction spectrum (XRPD spectrum) thereof is shown in FIG. 10. The DSC-TGA spectrum is shown in FIG. 11, having a sharp melting endothermic peak at 144.79° C. The crystal form was defined as crystal form A.

Example 17

The sample of crystal form I of the compound of formula (I) prepared in Example 2 and the sample of crystal form II prepared in Example 3 were spread flat in the air respectively to test the stability under conditions of lighting (4500 Lux), heating (40° C., 60° C.), and high humidity (RH 75%, RH 90%). Samplings were carried out on Day 5 and Day 10. The purity as detected by HPLC is shown in Table 1.

TABLE 1

Stability comparison of the samples of crystal
forms I and II of the compound of formula (I)

| Sample name | Time (day) | Lighting | 40° C. | 60° C. | RH 75% | RH 90% |
|---|---|---|---|---|---|---|
| Crystal form I | 0 | 99.67% | 99.67% | 99.67% | 99.67% | 99.67% |
|  | 5 | 99.54% | 99.52% | 99.55% | 99.53% | 99.59% |
|  | 10 | 99.34% | 99.45% | 99.39% | 99.39% | 99.43% |
| Crystal form II | 0 | 99.47% | 99.47% | 99.47% | 99.47% | 99.47% |
|  | 5 | 99.23% | 99.38% | 99.22% | 99.30% | 99.30% |
|  | 10 | 98.62% | 99.15% | 98.87% | 99.10% | 99.10% |

The results of the stability study showed that the stability of the sample of crystal form I of the compound of formula (I) was significantly better than that of the sample of crystal form II when they were spread flat in the air respectively under conditions of lighting, high temperature and high humidity.

Example 18

Crystal form I of the compound of formula (I) prepared according to the method of Example 2 was ground, heated and tableted. The results showed that the crystal form was stable. The detailed experimental data are shown in Table 2 below.

TABLE 2

Special stability study of crystal form I of the compound of formula (I)

| Sample | Treatment Process | Experimental procedure | Crystal form | DSC peak |
|---|---|---|---|---|
| Crystal form I | Grinding treatment for 10 minutes | 1 g of the sample of crystal form I of the compound of formula (I) was ground for 10 minutes in a mortar under nitrogen atmosphere. | Crystal form I | 214.17° C. |
| Crystal form I | Heating treatment for 3 hours at 80° C. | 1 g of the sample of crystal form I of the compound of formula (I) was spread flat and heated at 80° C. for 3 hours. | Crystal form I | 214.40° C. |
| Crystal form I | Tableting treatment | The sample of crystal form I of the compound of formula (I) was tableted. | Crystal form I | 214.44° C. |

Example 19. Pharmacokinetics Assay of Crystal Form 2 of the Malate of the Present Invention and Free Form in Rats SD rats were used as test animals. The drug concentration in plasma at different time points was determined by LC/MS/MS method after intragastrical administration of the crystal form 2 of the malate of the present invention and free form. The pharmacokinetic behavior and property of the crystal form 2 of the malate of the present invention and free form were studied and evaluated in SD rats.

Samples: crystal form 2 of the malate of the present invention and free form (the product of Example 1), prepared according to the methods of Examples 14 and 1.

Test animals: 8 healthy SD rats, half male and half female, were divided in two groups, and purchased from SINO-BRITSH SIPPR/BK LAB. ANIMAL LTD., CO, with certificate No.: SOCK (Shanghai) 2008-0016.

Preparation of the test compounds: the test compounds were added to 0.5% CMC-Na to prepare 0.5 mg/mL homogeneous suspensions for oral administration by ultrasound.

Administration: after an overnight fasting, 8 healthy SD rats, half male and half female, were administered the test compounds intragastrically at an administration volume of 10 mL/kg.

Method:

After an overnight fasting, 8 healthy SD rats, half male and half female, were administered the test compounds intragastrically. Blood samples (0.1 mL) were taken by jugular vein puncture before administration and at 0.5, 1, 2, 4, 6, 8, 12, and 24 hours after administration, and heparin sodium was used as an anticoagulant. The blood samples were centrifuged for 10 minutes at 3,500 rpm to separate the blood plasma, which was stored at −20° C. The content of the test compound in the plasma of SD rats after intragastric administration was determined by LC/MS/MS method.

Experimental Results

TABLE 3

Results of pharmacokinetics assay in SD rats (po: 5.0 mg/kg)

| Test sample | $T_{1/2}$ (h) | $AUC_{last}$ (ng/mL h*) | $Cl/F_{obs}$ (mL/min/kg) | $Vz/F_{obs}$ (mL/kg) |
|---|---|---|---|---|
| Crystal form 2 of the malate | 5.24 | 13365 | 6.87 | 3089 |
| Free form | 3.62 | 9283 | 9.82 | 3019 |

Among them, $T_{1/2}$ refers to half-life, $AUC_{last}$ refers to area under curve (0→t), Cl/F refers to clearance, and Vz/F refers to apparent distribution volume.

Experimental Conclusion

It can be seen from the results in Table 3 that compared to the free form, the crystal form 2 of the malate of the present invention has longer half-life, lower clearance, and higher exposure dose, indicating that the crystal form 2 of the malate of the present invention has good pharmacokinetic properties.

What is claimed is:

1. Crystal form I of the compound of formula (I), characterized by an X-ray powder diffraction spectrum comprising diffraction peaks at diffraction angles 2θ±0.2 of 3.49, 10.22, 12.27, 13.69, 15.46, 16.98, 18.04, 19.45, 23.95, and 29.44,

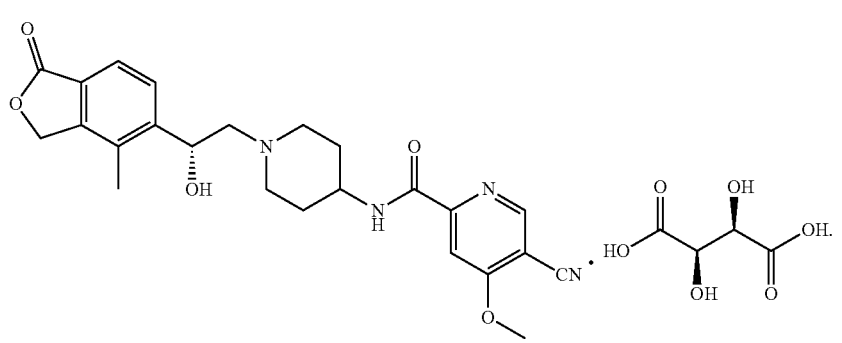

2. The crystal form I of the compound of formula (I) according to claim 1, characterized by an X-ray powder diffraction spectrum comprising diffraction peaks at diffraction angles 2θ±0.2 of 3.49, 10.22, 12.27, 13.69, 15.46, 16.98, 18.04, 19.45, 20.89, 23.95, 25.63, 26.71, and 29.44.

3. The crystal form I of the compound of formula (I) according to claim 1, wherein the crystal form I has a characteristic X-ray powder diffraction spectrum as shown in FIG. 1.

4. A pharmaceutical composition comprising the crystal form I according to claim 1 and a pharmaceutically acceptable carrier.

5. A pharmaceutical composition comprising the crystal form I according to claim 2 and a pharmaceutically acceptable carrier.

6. A pharmaceutical composition comprising the crystal form I according to claim 3 and a pharmaceutically acceptable carrier.

* * * * *